United States Patent
Brazeau et al.

(10) Patent No.: US 8,551,742 B2
(45) Date of Patent: Oct. 8, 2013

(54) COMPOSITIONS AND METHODS OF PRODUCING METHIONINE

(75) Inventors: Brian Brazeau, Oskaloosa, IA (US); Jin-Sook Chang, Seoul (KR); Kwang Myung Cho, Gyeonggi-do (KR); Young Wook Cho, Seoul (KR); Mervyn Desouza, Plymouth, MN (US); Holly J. Jessen, Chanhassen, MN (US); So-Young Kim, Gyeonggi-do (KR); Wei Niu, Spring Park, MN (US); Fernando A. Sanchez-Riera, Eden Prairie, MN (US); Yong-Uk Shin, Gyeonggi-do (KR); Hyewon Um, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 228 days.

(21) Appl. No.: 12/595,817

(22) PCT Filed: Apr. 11, 2007

(86) PCT No.: PCT/US2007/009146
§ 371 (c)(1),
(2), (4) Date: Oct. 13, 2009

(87) PCT Pub. No.: WO2008/127240
PCT Pub. Date: Oct. 23, 2008

(65) Prior Publication Data
US 2011/0183383 A1    Jul. 28, 2011

(51) Int. Cl.
*C12P 13/12* (2006.01)
*C12N 1/20* (2006.01)

(52) U.S. Cl.
USPC ..................................... 435/113; 435/252.33

(58) Field of Classification Search
None
See application file for complete search history.

(56) References Cited

U.S. PATENT DOCUMENTS

| | | | |
|---|---|---|---|
| 7,195,897 B2 | 3/2007 | Leonhartsberger et al. | |
| 7,371,551 B1 | 5/2008 | Leonhartsberger et al. | |
| 7,611,873 B1 | 11/2009 | Usuda et al. | |
| 2002/0049305 A1 | 4/2002 | Bathe et al. | |
| 2005/0054060 A1 | 3/2005 | Chateau et al. | |
| 2008/0286840 A1* | 11/2008 | Figge et al. .................. | 435/106 |

FOREIGN PATENT DOCUMENTS

| | | |
|---|---|---|
| JP | 2000-139471 A | 5/2000 |
| JP | 2006-516092 A | 6/2006 |
| WO | WO 02/18613 A1 | 3/2002 |
| WO | WO 2004/035617 A2 | 4/2004 |
| WO | WO 2004/038013 A2 | 5/2004 |
| WO | WO 2004/069996 A2 | 8/2004 |
| WO | WO 2004/108894 A2 | 12/2004 |
| WO | WO 2005/108561 A2 | 11/2005 |
| WO | WO 2006/065095 A1 | 6/2006 |
| WO | WO 2006/082254 A2 | 8/2006 |
| WO | WO 2006/138689 A2 | 12/2006 |
| WO | WO 2007/011845 A2 | 1/2007 |
| WO | WO 2007/011939 A2 | 1/2007 |

OTHER PUBLICATIONS

Whisstock et al. Qut Rev of Biophy. 2003, 36, pp. 307-340.*
Hwang, B-J., et al., "*Corynebacterium glutamicum* Utilizes both Transsulfuration and Direct Sulfhydrylation Pathways for Methionine Biosynthesis,"*J. Bacterial 184*(5):1277-86, American Sociaty for Microbiology, US (2002).
Auger, S., et al., "The *metIC* operon involved in methionine biosynthesis in *Bacillus subtilis* is controlled by transcription antitermination," *Microbiology 148*(Pt 2):507-18, Society for General Microbiology (SGM), Great Britain (Feb. 2002).
Belfaiza, J., et al., "Direct sulfhydrylation for methionine biosynthesis in *Leptospira meyeri*," *J. Bacteriol. 180*(2):250-5, American Society for Microbiology, United States (Jan. 1998).
Foglino, M., et al., "A direct sulfhydrylation pathway is used for methionine biosynthesis in *Pseudomonas aeruginosa*," *Microbiology 141* (Pt 2):431-9, Society for General Microbiology (SGM), Great Britain (Feb. 1995).
Gomes, J. and Kumar, D., "Production of L-methionine by submerged fermentation: A review," *Enzyme Microb. Technol. 37*(1):3-18, Elsevier Inc., United States (Jun. 2005).
Hacham, Y., et al., "In vivo analysis of various substrates utilized by cystathionine γ-synthase and *O*-acetylhomoserine sulfhydrylase in methionine biosynthesis," Mol. Biol Evol. 20(9)1 513-20, Society for Molecular Biology and Evolution, United States (Sep. 2003; Epub: Jun. 2003).
Hwang, B.J., et al., "*Corynebacterium glutamicum* utilizes both transsulfuration and direct sulfhydrylation pathways for methionine biosynthesis," *J. Bacteriol. 184*(5):1277-86, American Society for Microbiology, United States (Mar. 2002).
Inoue, H., et al., "Molecular characterization of the mde operon involved in L-methionine catabolism of *Pseudomonas putida*," *J. Bacteriol. 179*(12):3956-62, American Society for Microbiology, United States (Jun. 1997).
Krömer, J.O., et al., "Metabolic pathway analysis for rational design of L-methionine production by *Escherichia coli* and *Corynebacterium glutamicum*," *Metab. Eng. 8*(4):353-369, Elsevier Inc., England (Jul. 2006).
Kumar, D. and Gomes, J., et al., "Methionine production by fermentation," *Biotechnol Adv. 23*(1):41-61, Elsevier Inc., England (Jan. 2005).
Lee, H.S. and Hwang, B.J., "Methionine biosynthesis and its regulation in *Corynebacterium glutamicum*: parallel pathways of transsulfuration and direct sulfhydrylation," *Appl. Microbiol. Biotechnol. 62*(5-6):459-67, Springer-Verlag, Germany (Oct. 2003; Epub: Jul. 2003).

(Continued)

*Primary Examiner* — Tekchand Saidha
*Assistant Examiner* — Younus Meah
(74) *Attorney, Agent, or Firm* — Sterne, Kessler, Goldstein & Fox P.L.L.C.

(57) ABSTRACT

Described herein are microorganisms that produce methionine and related products from endogenous genes in a transsulfuration pathway, as well as from exogenous genes providing a direct sulfhydrylation pathway. Novel genes that are useful for methionine and SAMe production are disclosed.

12 Claims, 6 Drawing Sheets

(56) References Cited

OTHER PUBLICATIONS

Lee, L.W., et al., "Multimetabolite control of a biosynthetic pathway by sequential metabolites," *J. Biol. Chem.* 241(22):5479-80, American Society for Biochemistry and Molecular Biology, United States (Nov. 1966).

Picardeau, M., et al., "Genetic evidence for the existence of two pathways for the biosynthesis of methionine in the *Leptospira* spp," *FEMS Microbiol Lett.* 225(2):257-62, Elsevier B.V., Netherlands (Aug. 2003).

Vermeij, P., and Kertesz, M.A., "Pathways of assimilative sulfur metabolism in *Pseudomonas putida*," *J. Bacteriol.* 181(18):5833-37, American Society for Microbiology, United States (Sep. 1999).

International Search Report for International Patent Publication No. PCT/US2007/009146, European Patent Office, Rijswijk, Netherlands, mailed Mar. 27, 2008.

Written Opinion of the International Searching Authority for International Patent Publication No. PCT/US2007/009146, European Patent Office, Rijswijk, Netherlands, mailed Mar. 27, 2008.

Coe, D.M., and Viola, R.E., "Assessing the roles of essential functional groups in the mechanism of homoserine succinyltransferase," *Archives of Biochemistry and Biophysics* 461:211-218, Elsevier Inc., United States (May 2007).

Rosen, R., et al., "Probing the active site of homoserine *trans*-succinylast," *FEBS Letters* 577:386-392, Federation of European Biochemical Societies, Elsevier B.V., Netherlands (2004).

Usuda, Y., and Kurahashi, O., "Effects of Deregulation of Methionine Biosynthesis on Methionine Excretion Microbiology Excretion in *Escherichia coli*," *Applied and Environmental Microbiology* 71(6):3228-3234, American Society for Microbiology, United States (2005).

Bourhy, P., et al., "Homoserne *O*-Acetyltransferase, Involved in the *Leptospira meyeri* Methionine Biosynthetic Pathway, is not Feedback Inhibited," *Journal of Bacteriology* 179(13):4396-4398, American Society for Microbiology (1997).

NCBI Entrez, GenBank Report, Accession No. AAC76983, Blattner, F.R., et al., Entry Date Sep. 8, 2006.

Extended European Search Report for EP Application No. 12165779.5, The Hague, Netherlands, mailed on Jan. 21, 2013, 17 pages.

Office Action for Japanese Patent Application No. 2010-502984, Japan Patent Office, Tokyo, Japan, issued Feb. 12, 2013, 6 pages.

English language translation of Office Action for Japanese Patent Application No. 2010-502984, 7 pages.

English language abstract of Japanese Patent Publication No. 2000-139471 A.

Office Action for Japanese Patent Application No. 2010-502984, Dated Mar. 19, 2012, Japanese Patent Office, Japan, 6 pages.

English language translation of Office Action for Japanese Patent Application No. 2010-502984, Dated Mar. 19, 2012, Hanol Intellectual Property and Law, Republic of Korea, 5 pages.

\* cited by examiner

```
                              SEQUENCE LISTING

<160> NUMBER OF SEQ ID NOS: 47

<210> SEQ ID NO 1
<211> LENGTH: 930
<212> TYPE: DNA
<213> ORGANISM: Escherichia coli

<400> SEQUENCE: 1
atgccgattc gtgtgccgga cgagctaccc gccgtcaatt tcttgcgtga agaaaacgtc      60
tttgtgatga caacttctcg tgcgtctggt caggaaattc gtccgcttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggctggtgg agtttaatga tgtcgcttac      360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaacaac tctctggcgt ttacgagcat catattctcc atcctcatgc gcttctgacg     540
cgtggctttg atgattcatt cctggcaccg cattcgcgct atgctgactt tccggctgcg     600
ttgattcgtg attacaccga tctggaaatt ctggcagaga cggaagaagg ggatgcatat     660
ctgttagcca gtaaagataa gcgcattgcc tttgtgacgg gccatcccga atatgatgcg     720
caaacgctgg cgcaggaatt tttccgcgat gtggaagccg gactagaccc ggatgtaccg     780
tataactatt tcccgcacaa tgatccgcaa aatacaccgc gagcgagctg gcgtagtcac     840
ggtaatttac tgtttaccaa ctggctcaac tattacgtct accggatcac gccatacgat     900
ctacggcaca tgaatccaac gctggattaa                                      930

<210> SEQ ID NO 2
<211> LENGTH: 309
<212> TYPE: PRT
<213> ORGANISM: Escherichia coli

<400> SEQUENCE: 2

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125
```

```
Glu Trp Ser Lys Asp His Val Thr Ser Thr Leu Phe Val Cys Trp Ala
            130                 135                 140

Val Gln Ala Ala Leu Asn Ile Leu Tyr Gly Ile Pro Lys Gln Thr Arg
145                 150                 155                 160

Thr Glu Gln Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Gly Asp Ala Tyr Leu Leu Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Arg Ile Thr Pro Tyr Asp Leu Arg His Met
290                 295                 300

Asn Pro Thr Leu Asp
305

<210> SEQ ID NO 3
<211> LENGTH: 930
<212> TYPE: DNA
<213> ORGANISM: Escherichia coli

<400> SEQUENCE: 3
atgccgattc gtgtgccgga cgagctaccc gccgtcaatt tcttgcgtga agaaaacgtc    60
tttgtgatgt caacttctcg tgcgtctggt caggaaattc gtccacttaa ggttctgatc   120
cttaacctga tgccgaagaa gattgaaact gaaaatcagt ttctgcgcct gctttcaaac   180
tcacctttgc aggtcgatat tcagctgttg cgcatcgatt ctcgtgaatc gcgcaacacg   240
cccgcagagc atctgaacaa cttctactgt aactttgaag atattcagga tcagaacttt   300
gacggtttga ttgtaactgg tgcgccgctg ggcctggtgg agtttaatga tgtcgcttac   360
tggccgcaga tcaaacaggt gctggagtgg tcgaaagatc acgtcacctc gacgctgttt   420
gtctgctggg cggtacaggc cgcgctcaat atcctctacg gcattcctaa gcaaactcgc   480
accgaaaaac tctctggcgt ttacgagcat catattctcc atcctcatgc gcttctgacg   540
cgtggctttg atgattcatt cctggcaccg cattcgcgct atgctgactt ccggcagcg   600 ttgattcgtg attacaccga tctggaaatt ctggcagaga cggaagaagg ggatgcatat   660
ctgtttgcca gtaaagataa gcgcattgcc tttgtgacgg gccatccgga atatgatgcg   720
caaacgctgg cgcaggaatt tttccgcgat gtggaagccg gactagaccc ggatgtaccg   780
tataactatt tcccgcacaa tgatccgcaa aatacaccgc gagagagctg gcgtagtcac   840
ggtaatttac tgtttaccaa ctggctcaac tattacgtct accagatcgc gccatacgat   900
ctacggcaca tgtatccaac gctggattaa                                    930
```

<210> SEQ ID NO 4
<211> LENGTH: 309
<212> TYPE: PRT
<213> ORGANISM: Escherichia coli

<400> SEQUENCE: 4

Met Pro Ile Arg Val Pro Asp Glu Leu Pro Ala Val Asn Phe Leu Arg
1               5                   10                  15

Glu Glu Asn Val Phe Val Met Ser Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Glu Ser Trp Arg Ser His Gly Asn Leu Leu Phe Thr Asn Trp
        275                 280                 285

Leu Asn Tyr Tyr Val Tyr Gln Ile Ala Pro Tyr Asp Leu Arg His Met
    290                 295                 300

Tyr Pro Thr Leu Asp
305

<210> SEQ ID NO 5
<211> LENGTH: 930
<212> TYPE: DNA
<213> ORGANISM: Escherichia coli

<400> SEQUENCE: 5
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180

```
tcacctttgc aggtcgatat tcagctgttg cgcatcgatt cccgtgaatc gcgcaacacg      240
cccgcagagc atctgaacaa cttctactgt aactttgaag atattcagga tcagaacttt      300
gacggtttga ttgtaactgg tgcgccgctg ggcctggtgg agtttaatga tgtcgcttac      360
tggccgcaga tcaaacaggt gctggagtgg tcgaaagatc acgtcacctc gacgctgttt      420
gtctgctggg cggtacaggc cgcgctcaac atcctctacg gcattcctaa gcaaactcgc      480
accgaaaaac tctctggcgt ttacgagcat catattctcc atcctcatgc gcttctgacg      540
cgtggctttg atgattcatt cctggcaccg cattcgcgct atgctgactt tccggcagcg      600
ttgattcgtg attacaccga tctggaaatt ctggcagaga cggaagaagg ggatgcatat      660
ctgtttgcca gtaaagataa gcgcattgcc tttgtgacgg gccatcccga atatgatgcg      720
caaacgctgg cgcaggaatt tttccgcgat gtggaagccg actagaccc ggatgtaccg       780 tataactatt tcccgcacaa tgatccgcaa atacaccgc gagcgagctg cgtagtcac       840 ggtaatttac tgtttaccaa ctggctccac tattacgtct accagatcac gccatacgat      900
ctacggcaca tgaatccaac gctggattaa                                       930

<210> SEQ ID NO 6
<211> LENGTH: 309
<212> TYPE: PRT
<213> ORGANISM: Escherichia coli

<400> SEQUENCE: 6

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Ser Asn Ser Pro Leu Gln
        50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240
```

```
Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu His Tyr Tyr Val Tyr Gln Ile Thr Pro Tyr Asp Leu Arg His Met
    290                 295                 300

Asn Pro Thr Leu Asp
305

<210> SEQ ID NO 7
<211> LENGTH: 930
<212> TYPE: DNA
<213> ORGANISM: Escherichia coli

<400> SEQUENCE: 7
atgccgattc gtgtgccgga cgagctaccc gccgtcaatt tcttgcgtga agaaaacgtc      60
tttgtgatga caacttctcg tgcgcctggt caggaaattc gtccacttaa ggttctgatc     120
cttaacctga tgccgaagaa gattgaaact gaaaatcagt ttctgcgcct gctttcaaac     180 tcaccttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg ggtttaatga tgtcgcttac     360
tggccgcaga tcaaacaggt gctggagtgg tcgaaagatc acgtcacctc gacgctgtct     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt ccggcagcg     600 ttgattcgtg attacaccga tctggaaatt ctggcagaga cggaagaagg ggatgcatat     660
ctgtttgcca gtaaagataa gcgcattgcc tttgtgacgg ccatcccga atatgatgcg     720 caaacgctgg cgcaggaatt tttccgcgat gtggaagccg actagaccc ggatgtaccg     780 tataactatt tcccgcacaa tgatccgcaa aatacaccgc gagcgagctg gcgtagtcac     840
ggtaatttac tgtttaccaa ctggctcaac tattacgtct accagatcac gccatacgat     900
ctacggcaca tgaacccaac gctggattaa                                      930

<210> SEQ ID NO 8
<211> LENGTH: 309
<212> TYPE: PRT
<213> ORGANISM: Escherichia coli

<400> SEQUENCE: 8

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Pro Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95
```

```
Asp Gln Asn Phe Asp Gly Leu Ile Val Thr Gly Ala Pro Leu Gly Leu
                100                 105                 110

Val Gly Phe Asn Asp Val Ala Tyr Trp Pro Gln Ile Lys Gln Val Leu
            115                 120                 125

Glu Trp Ser Lys Asp His Val Thr Ser Thr Leu Ser Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 9
<211> LENGTH: 930
<212> TYPE: DNA
<213> ORGANISM: Escherichia coli

<400> SEQUENCE: 9
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcagcacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgatt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cactcgcgct atgctgactt ccggcagcg      600 ttgattcgtg attacaccga tctgaaaatt ctggcagaga cggaagaagg ggatgcatat     660
ctgtttgcca gtaaagataa gcgcattgcc tttgtgacgg ccatcccgaa atatgatgcg     720
caaacgctgg cgcaggaatt tttccgcgat gtggaagccg actagacccc ggatgtaccg     780
tataactatt tcccgcacaa tgatccgcaa aatacaccgc gagcgagctg gcgtagtcac     840
ggtaatttac tgtttaccaa ctggctcaac aattacgtct accagatcac gccatacgat     900
```
ctacggcact tgaatccaac gctggattaa                                   930

<210> SEQ ID NO 10
<211> LENGTH: 309
<212> TYPE: PRT
<213> ORGANISM: Escherichia coli

<400> SEQUENCE: 10

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Ser Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Ile Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Asn Tyr Val Tyr Gln Ile Thr Pro Tyr Asp Leu Arg His Leu
    290                 295                 300

Asn Pro Thr Leu Asp
305

<210> SEQ ID NO 11
<211> LENGTH: 28
<212> TYPE: DNA
<213> ORGANISM: Artificial Sequence
<220> FEATURE:
<223> OTHER INFORMATION: PCR primer

<400> SEQUENCE: 11
gctagccatg gttaaagttt atgccccg                                          28

<210> SEQ ID NO 12
<211> LENGTH: 29
<212> TYPE: DNA
<213> ORGANISM: Artificial Sequence
<220> FEATURE:
<223> OTHER INFORMATION: PCR primer

<400> SEQUENCE: 12
gagctcttag ttttccagta ctcgtgcgc                                         29

<210> SEQ ID NO 13
<211> LENGTH: 71
<212> TYPE: DNA
<213> ORGANISM: Artificial Sequence
<220> FEATURE:
<223> OTHER INFORMATION: PCR primer

<400> SEQUENCE: 13
atggctgaat ggagcggcga atatatcagc ccatacgctg agcacggcaa ggtgtaggct       60
ggagctgctt c                                                            71

<210> SEQ ID NO 14
<211> LENGTH: 65
<212> TYPE: DNA
<213> ORGANISM: Artificial Sequence
<220> FEATURE:
<223> OTHER INFORMATION: PCR primer

<400> SEQUENCE: 14
gtattcccac gtctccgggt taatccccat ctcacgcatg atctccatat gaatatcctc       60
cttag                                                                   65

<210> SEQ ID NO 15
<211> LENGTH: 19
<212> TYPE: DNA
<213> ORGANISM: Artificial Sequence
<220> FEATURE:
<223> OTHER INFORMATION: PCR primer

<400> SEQUENCE: 15
gggctttgtc ggtgaaatg                                                    19

<210> SEQ ID NO 16
<211> LENGTH: 19
<212> TYPE: DNA
<213> ORGANISM: Artificial Sequence
<220> FEATURE:
<223> OTHER INFORMATION: PCR primer

<400> SEQUENCE: 16
actttgcgat gagcgagag                                                    19

<210> SEQ ID NO 17
<211> LENGTH: 27
<212> TYPE: DNA
<213> ORGANISM: Artificial Sequence
<220> FEATURE:
<223> OTHER INFORMATION: PCR primer

<400> SEQUENCE: 17
gctagccatg agcttttttc acgccag                                           27

```
<210> SEQ ID NO 18
<211> LENGTH: 26
<212> TYPE: DNA
<213> ORGANISM: Artificial Sequence
<220> FEATURE:
<223> OTHER INFORMATION: PCR primer

<400> SEQUENCE: 18
gagctcttat aaaccaggtc gaaccc                                         26

<210> SEQ ID NO 19
<211> LENGTH: 26
<212> TYPE: DNA
<213> ORGANISM: Artificial Sequence
<220> FEATURE:
<223> OTHER INFORMATION: PCR primer

<400> SEQUENCE: 19
cagctgatga gcttttttca cgccag                                         26

<210> SEQ ID NO 20
<211> LENGTH: 26
<212> TYPE: DNA
<213> ORGANISM: Artificial Sequence
<220> FEATURE:
<223> OTHER INFORMATION: PCR primer

<400> SEQUENCE: 20
aagcttttat aaaccaggtc gaaccc                                         26

<210> SEQ ID NO 21
<211> LENGTH: 32
<212> TYPE: DNA
<213> ORGANISM: Artificial Sequence
<220> FEATURE:
<223> OTHER INFORMATION: PCR primer

<400> SEQUENCE: 21
cggggtacca ccgcgggctt attccattac at                                  32

<210> SEQ ID NO 22
<211> LENGTH: 32
<212> TYPE: DNA
<213> ORGANISM: Artificial Sequence
<220> FEATURE:
<223> OTHER INFORMATION: PCR primer

<400> SEQUENCE: 22
acgcgatatc ttaatctcct agattgggtt tc                                  32

<210> SEQ ID NO 23
<211> LENGTH: 28
<212> TYPE: DNA
<213> ORGANISM: Artificial Sequence
<220> FEATURE:
<223> OTHER INFORMATION: PCR primer

<400> SEQUENCE: 23
cggggtacct ggttacaaca acgcctgg                                       28

<210> SEQ ID NO 24
<211> LENGTH: 29
<212> TYPE: DNA
<213> ORGANISM: Artificial Sequence
<220> FEATURE:
<223> OTHER INFORMATION: PCR primer

<400> SEQUENCE: 24
```

```
catgatatct acctcgttac ctttggtcg                                      29
```

<210> SEQ ID NO 25
<211> LENGTH: 70
<212> TYPE: DNA
<213> ORGANISM: Artificial Sequence
<220> FEATURE:
<223> OTHER INFORMATION: PCR primer

<400> SEQUENCE: 25

```
ttactctggt gcctgacatt tcaccgacaa agcccaggga acttcatcac gtgtaggctg    60
gagctgcttc                                                          70
```

<210> SEQ ID NO 26
<211> LENGTH: 69
<212> TYPE: DNA
<213> ORGANISM: Artificial Sequence
<220> FEATURE:
<223> OTHER INFORMATION: PCR primer

<400> SEQUENCE: 26

```
ttacccctig tttgcagccc ggaagccatt ttccaggtcg gcaattaaat catatgaata    60
tcctcctta                                                           69
```

<210> SEQ ID NO 27
<211> LENGTH: 71
<212> TYPE: DNA
<213> ORGANISM: Artificial Sequence
<220> FEATURE:
<223> OTHER INFORMATION: PCR primer

<400> SEQUENCE: 27

```
caatttcttg cgtgaagaaa acgtctttgt gatgacaact tctcgtgcgt gtgtaggctg    60
gagctgcttc c                                                        71
```

<210> SEQ ID NO 28
<211> LENGTH: 70
<212> TYPE: DNA
<213> ORGANISM: Artificial Sequence
<220> FEATURE:
<223> OTHER INFORMATION: PCR primer

<400> SEQUENCE: 28

```
aatccagcgt tggattcatg tgccgtagat cgtatggcgt gatctggtag catatgaata    60
tcctccttag                                                          70
```

<210> SEQ ID NO 29
<211> LENGTH: 28
<212> TYPE: DNA
<213> ORGANISM: Artificial Sequence
<220> FEATURE:
<223> OTHER INFORMATION: PCR primer

<400> SEQUENCE: 29

```
aatggatcct gccgtgagcg gcgaatac                                       28
```

<210> SEQ ID NO 30
<211> LENGTH: 28
<212> TYPE: DNA
<213> ORGANISM: Artificial Sequence
<220> FEATURE:
<223> OTHER INFORMATION: PCR primer

<400> SEQUENCE: 30

-continued

```
agctctagac tgctgaggta cgtttcgg                                        28

<210> SEQ ID NO 31
<211> LENGTH: 20
<212> TYPE: DNA
<213> ORGANISM: Artificial Sequence
<220> FEATURE:
<223> OTHER INFORMATION: PCR primer

<400> SEQUENCE: 31
cgaagtaatc gcaacatccg                                                 20

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
gtctgctatg tggtgctatc                                                 20

<210> SEQ ID NO 33
<211> LENGTH: 31
<212> TYPE: DNA
<213> ORGANISM: Artificial Sequence
<220> FEATURE:
<223> OTHER INFORMATION: PCR primer

<400> SEQUENCE: 33
gccaggatcc gatgacgcgt aaacaggcca c                                    31

<210> SEQ ID NO 34
<211> LENGTH: 30
<212> TYPE: DNA
<213> ORGANISM: Artificial Sequence
<220> FEATURE:
<223> OTHER INFORMATION: PCR primer

<400> SEQUENCE: 34
ccgcaagctt tttacccctt gtttgcagcc                                      30

<210> SEQ ID NO 35
<211> LENGTH: 309
<212> TYPE: PRT
<213> ORGANISM: Escherichia coli

<400> SEQUENCE: 35

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110
```

```
Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Ser Phe Leu Ala Pro His Ser
                180                 185                 190

Arg Tyr Ala Asp Phe Pro Ala Ala Leu Ile Arg Asp Tyr Thr Asp Leu
                195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
                260                 265                 270

Pro Arg Ala Ser Trp Arg Ser His Gly Asn Leu Leu Phe Thr Asn Trp
                275                 280                 285

Leu Asn Tyr Tyr Val Tyr Gln Ile Thr Pro Tyr Asp Leu Arg His Met
                290                 295                 300

Asn Pro Thr Leu Asp
305

<210> SEQ ID NO 36
<211> LENGTH: 425
<212> TYPE: PRT
<213> ORGANISM: Pseudomonas aeruginosa

<400> SEQUENCE: 36

Met Lys Leu Glu Thr Leu Ala Val His Ala Gly Tyr Ser Pro Asp Pro
1               5                   10                  15

Thr Thr Arg Ala Val Ala Val Pro Ile Tyr Gln Thr Thr Ser Tyr Ala
                20                  25                  30

Phe Asp Asp Thr Gln His Gly Ala Asp Leu Phe Asp Leu Lys Val Pro
            35                  40                  45

Gly Asn Ile Tyr Thr Arg Ile Met Asn Pro Thr Asn Asp Val Leu Glu
50                  55                  60

Gln Arg Val Ala Ala Leu Glu Gly Gly Val Gly Ala Leu Ala Val Ala
65                  70                  75                  80

Ser Gly Met Ala Ala Ile Thr Tyr Ala Ile Gln Thr Val Ala Glu Ala
                85                  90                  95

Gly Asp Asn Ile Val Ser Val Ala Lys Leu Tyr Gly Gly Thr Tyr Asn
                100                 105                 110

Leu Leu Ala His Thr Leu Pro Arg Ile Gly Ile Gln Ala Arg Phe Ala
            115                 120                 125

Ala His Asp Asp Val Ala Ala Leu Glu Ala Leu Ile Asp Glu Arg Thr
130                 135                 140

Lys Ala Val Phe Cys Glu Thr Ile Gly Asn Pro Ala Gly Asn Ile Ile
145                 150                 155                 160

Asp Leu Gln Ala Leu Ala Asp Ala Ala His Arg His Gly Val Pro Leu
                165                 170                 175
```

```
Ile Val Asp Asn Thr Val Ala Thr Pro Val Leu Cys Arg Pro Phe Glu
            180                 185                 190

His Gly Ala Asp Ile Val Val His Ser Leu Thr Lys Tyr Met Gly Gly
            195                 200                 205

His Gly Thr Ser Ile Gly Gly Ile Val Val Asp Ser Gly Lys Phe Asp
210                 215                 220

Trp Ala Ala Asn Lys Ser Arg Phe Pro Leu Leu Asn Thr Pro Asp Pro
225                 230                 235                 240

Ser Tyr His Gly Val Thr Tyr Thr Glu Ala Phe Gly Pro Ala Ala Phe
                245                 250                 255

Ile Gly Arg Cys Arg Val Val Pro Leu Arg Asn Met Gly Ala Ala Leu
            260                 265                 270

Ser Pro Phe Asn Ala Phe Leu Ile Leu Gln Gly Leu Glu Thr Leu Ala
            275                 280                 285

Leu Arg Met Glu Arg His Cys Asp Asn Ala Leu Ala Val Ala Arg Tyr
            290                 295                 300

Leu Gln Gln His Pro Gln Val Ala Trp Val Lys Tyr Ala Gly Leu Ala
305                 310                 315                 320

Asp Asn Pro Glu His Ala Leu Ala Arg Arg Tyr Leu Gly Gly Arg Pro
                325                 330                 335

Ala Ala Ile Leu Ser Phe Gly Ile Gln Gly Gly Ser Ala Ala Gly Ala
            340                 345                 350

Arg Phe Ile Asp Ala Leu Lys Leu Val Val Arg Leu Val Asn Ile Gly
            355                 360                 365

Asp Ala Lys Ser Leu Ala Cys His Pro Ala Ser Thr Thr His Arg Gln
370                 375                 380

Leu Asn Ala Glu Glu Leu Ala Arg Ala Gly Val Ser Asp Asp Met Val
385                 390                 395                 400

Arg Leu Ser Ile Gly Ile Glu His Ile Asp Asp Ile Leu Ala Asp Leu
                405                 410                 415

Asp Gln Ala Leu Ala Ala Ala Arg
            420                 425

<210> SEQ ID NO 37
<211> LENGTH: 442
<212> TYPE: PRT
<213> ORGANISM: Leptospira meyeri

<400> SEQUENCE: 37

Met Val Gly Pro Ser Gly Glu Ser Met Pro Arg Asn Phe Lys Pro Glu
1               5                   10                  15

Thr Ile Ala Leu His Gly Gly Gln Glu Pro Asp Pro Thr Thr Thr Ser
            20                  25                  30

Arg Ala Val Pro Leu Tyr Gln Thr Thr Ser Tyr Val Phe Lys Asp Thr
            35                  40                  45

Asp His Ala Ala Arg Leu Phe Gly Leu Gln Glu Phe Gly Asn Ile Tyr
        50                  55                  60

Thr Arg Leu Met Asn Pro Thr Thr Asp Val Leu Glu Lys Arg Val Ala
65                  70                  75                  80

Ala Leu Glu Gly Gly Val Ala Ala Leu Ala Thr Ala Ser Gly Gln Ser
                85                  90                  95

Ala Glu Met Leu Ala Leu Leu Asn Ile Val Glu Ala Gly Gln Glu Ile
            100                 105                 110

Val Ala Ser Ser Ser Leu Tyr Gly Gly Thr Tyr Asn Leu Leu His Tyr
            115                 120                 125
```

```
Thr Phe Pro Lys Leu Gly Ile Lys Val His Phe Val Asp Gln Ser Asp
            130                 135                 140

Pro Glu Asn Phe Arg Lys Ala Ser Asn Asp Lys Thr Arg Ala Phe Tyr
145                 150                 155                 160

Ala Glu Thr Leu Gly Asn Pro Lys Leu Asp Thr Leu Asp Ile Ala Ala
                165                 170                 175

Val Ser Lys Val Ala Lys Glu Val Gly Val Pro Leu Val Ile Asp Asn
                180                 185                 190

Thr Met Pro Ser Pro Tyr Leu Val Asn Pro Leu Lys His Gly Ala Asp
            195                 200                 205

Ile Val Val His Ser Leu Thr Lys Phe Leu Gly Gly His Gly Thr Ser
210                 215                 220

Ile Gly Gly Ile Ile Ile Asp Gly Gly Ser Phe Asn Trp Gly Asn Gly
225                 230                 235                 240

Lys Phe Lys Asn Phe Thr Glu Pro Asp Pro Ser Tyr His Gly Leu Lys
                245                 250                 255

Phe Trp Glu Val Phe Gly Lys Phe Glu Pro Phe Gly Gly Val Asn Ile
                260                 265                 270

Ala Phe Ile Leu Lys Ala Arg Val Gln Gly Leu Arg Asp Leu Gly Pro
            275                 280                 285

Ala Ile Ser Pro Phe Asn Ala Trp Gln Ile Leu Gln Gly Val Glu Thr
290                 295                 300

Leu Pro Leu Arg Met Glu Arg His Ser Gly Asn Ala Leu Lys Val Ala
305                 310                 315                 320

Glu Phe Leu Gln Lys His Pro Lys Ile Glu Trp Val Asn Tyr Pro Gly
                325                 330                 335

Leu Ser Thr Asp Lys Asn Tyr Ala Thr Ala Lys Lys Tyr His Glu Arg
            340                 345                 350

Gly Leu Phe Gly Ala Ile Val Gly Phe Glu Ile Lys Gly Gly Val Glu
                355                 360                 365

Lys Ala Lys Lys Phe Ile Asp Gly Leu Glu Leu Phe Ser Leu Leu Ala
            370                 375                 380

Asn Ile Gly Asp Ala Lys Ser Leu Ala Ile His Pro Ala Ser Thr Thr
385                 390                 395                 400

His Gln Gln Leu Thr Gly Pro Glu Gln Ile Ser Ala Gly Val Thr Pro
                405                 410                 415

Gly Phe Val Arg Leu Ser Val Gly Leu Glu Asn Ile Asp Asp Ile Leu
            420                 425                 430

Val Asp Leu Glu Glu Ala Leu Lys Asn Ile
            435                 440

<210> SEQ ID NO 38
<211> LENGTH: 484
<212> TYPE: PRT
<213> ORGANISM: Chloroflexus aurantiacus

<400> SEQUENCE: 38

Met Arg Arg Arg Ile Arg Thr Val Leu Ser Pro Ala Glu Val Phe Trp
1               5                   10                  15

Lys Met Ser Asp Val Glu Glu Arg Leu Ser Ala Thr Ile Ser Arg Pro
                20                  25                  30

His Arg Thr Leu Arg Ala Phe Leu Leu Pro Ala Ile Trp Leu Ile Cys
            35                  40                  45

Phe Glu Glu Val Val Met Ser Asp Ala Pro Arg Phe Thr Gly Phe Glu
50                  55                  60
```

```
Thr Leu Ala Leu His Ala Gly Gln Thr Pro Asp Pro Thr Thr Gly Ser
 65                  70                  75                  80

Arg Ala Val Pro Ile Tyr Ala Thr Thr Ser Tyr Gln Phe Lys Asp Thr
                 85                  90                  95

Asp His Ala Ala Arg Leu Phe Asn Leu Gln Glu Phe Gly Asn Ile Tyr
            100                 105                 110

Thr Arg Ile Met Asn Pro Thr Thr Asp Val Phe Glu Gln Arg Met Ala
        115                 120                 125

Ala Leu Glu Gly Gly Val Gly Ala Leu Ala Leu Ala Ser Gly Gln Ala
    130                 135                 140

Ala Glu Thr Leu Ala Ile Leu Asn Leu Ala Gly Ser Gly Asp Asn Ile
145                 150                 155                 160

Val Ala Ser Ser Asp Leu Tyr Gly Gly Thr Tyr Asn Leu Phe Arg His
                165                 170                 175

Thr Leu Pro Lys Leu Gly Ile Thr Thr Arg Phe Val Asp Ala Arg Asp
            180                 185                 190

Tyr Asp Gly Phe Ala Ala Ala Ile Asp Gly Arg Thr Lys Ala Phe Phe
        195                 200                 205

Leu Glu Leu Val Gly Asn Pro Arg Leu Asp Val Leu Asp Leu Glu Arg
    210                 215                 220

Ile Ala Ala Ile Ala His Ala Gln Gly Val Pro Val Ile Val Asp Ala
225                 230                 235                 240

Thr Thr Val Thr Pro Tyr Leu Trp Gln Pro Ile Gln His Gly Ala Asp
                245                 250                 255

Ile Val Ile His Ser Ala Thr Lys Tyr Ile Gly Gly His Gly Thr Ala
            260                 265                 270

Ile Gly Gly Ile Ile Val Asp Ser Gly Lys Phe Asp Trp Ala Ala Ser
        275                 280                 285

Gly Arg Phe Pro Glu Phe Thr Asn Pro Asp Pro Ser Tyr His Gly Leu
    290                 295                 300

Ile Tyr Thr Gln Ala Phe Gly Asn Leu Ala Tyr Ile Ile Lys Ala Arg
305                 310                 315                 320

Val Gln Gly Leu Arg Asp Ile Gly Ala Ala Leu Ser Pro Phe Asn Ser
                325                 330                 335

Phe Leu Phe Leu Gln Gly Leu Glu Thr Leu Pro Leu Arg Met Glu Arg
            340                 345                 350

His Ser Lys Asn Ala Leu Ala Val Ala Arg Tyr Leu Ser Glu His Pro
        355                 360                 365

Lys Val Ala Trp Val Asn Tyr Pro Gly Leu Pro Ser His Pro Ser Tyr
    370                 375                 380

Ala Leu Ala Gln Lys Tyr Leu Pro Arg Gly Gln Ser Gly Ile Val Gly
385                 390                 395                 400

Phe Gly Leu Lys Gly Gly Arg Ala Ala Gly Arg Thr Phe Ile Glu Arg
                405                 410                 415

Leu Arg Leu Phe Ser His Leu Ala Asn Ile Gly Asp Ala Lys Ser Leu
            420                 425                 430

Ala Ile His Pro Ala Thr Thr His Ser Gln Leu Thr Pro Glu Glu
        435                 440                 445

Gln Leu Leu Thr Gly Val Thr Asp Asp Tyr Val Arg Leu Ser Ile Gly
    450                 455                 460

Leu Glu Thr Ile Asp Asp Ile Leu Ala Asp Leu Asp His Ala Leu Ala
465                 470                 475                 480

Gly Thr Pro Ser
```

-continued

<210> SEQ ID NO 39
<211> LENGTH: 434
<212> TYPE: PRT
<213> ORGANISM: Nostoc punctiforme

<400> SEQUENCE: 39

```
Met Ser Glu Gln Tyr Arg Phe Glu Thr Leu Gln Val His Ala Gly Gln
1               5                   10                  15

Glu Pro Ala Pro Gly Asn Asn Ala Arg Ala Val Pro Ile Tyr Gln Thr
            20                  25                  30

Thr Ser Tyr Val Phe Asp Asp Thr Glu His Gly Ala Arg Leu Phe Ala
        35                  40                  45

Leu Gln Glu Phe Gly Asn Ile Tyr Thr Arg Ile Met Asn Pro Thr Thr
    50                  55                  60

Asp Val Phe Glu Lys Arg Ile Ala Ala Leu Glu Gly Gly Val Ala Ala
65                  70                  75                  80

Leu Ala Thr Ala Ser Gly Gln Ala Ala Gln Phe Leu Ala Ile Ser Thr
                85                  90                  95

Ile Ala Gln Ala Gly Asp Asn Ile Val Ser Thr Ser Phe Leu Tyr Gly
            100                 105                 110

Gly Thr Tyr Asn Gln Phe Lys Val Ser Leu Pro Arg Leu Gly Ile Asn
        115                 120                 125

Val Lys Phe Val Glu Gly Asp Asp Pro Glu Ser Phe Arg Gln Ala Ile
130                 135                 140

Asp Ala Arg Thr Lys Ala Leu Tyr Val Glu Thr Ile Gly Asn Pro Gln
145                 150                 155                 160

Tyr Asn Ile Pro Asp Phe Ala Ala Leu Ala His Ile Ala His Glu Asn
                165                 170                 175

Gly Ile Pro Leu Ile Val Asp Asn Thr Phe Gly Ala Gly Gly Tyr Leu
            180                 185                 190

Ala Arg Pro Ile Glu His Gly Ala Asp Ile Val Val Gly Ser Ala Thr
        195                 200                 205

Lys Trp Ile Gly Gly His Gly Thr Ser Ile Gly Gly Val Ile Val Asp
    210                 215                 220

Ser Gly Lys Phe Asp Trp Gly Asn Gly Lys Phe Pro Leu Phe Thr Glu
225                 230                 235                 240

Pro Ala Pro Gly Tyr His Gly Leu Asn Phe Gln Glu Val Phe Gly Pro
                245                 250                 255

Ser Gly Ser Phe Gly Asn Ile Ala Phe Ile Ile Arg Ala Arg Val Glu
            260                 265                 270

Gly Leu Arg Asp Phe Gly Pro Ser Leu Ser Pro Phe Asn Ala Phe Leu
        275                 280                 285

Leu Leu Gln Gly Leu Glu Thr Leu Ser Leu Arg Val Asp Arg His Val
    290                 295                 300

Ser Asn Ala Leu Glu Leu Ala Arg Trp Leu Glu Gln Gln Glu Gln Val
305                 310                 315                 320

Leu Trp Val Asn Tyr Pro Gly Leu Pro Asn His Ser Tyr His Glu Arg
                325                 330                 335

Ala Lys Lys Tyr Leu Arg His Gly Phe Gly Gly Val Leu Asn Phe Gly
            340                 345                 350

Ile Lys Gly Gly Leu Glu Ala Gly Lys Ala Phe Ile Asn His Val Lys
        355                 360                 365

Leu Ala Ser His Leu Ala Asn Val Gly Asp Ala Lys Thr Leu Val Ile
    370                 375                 380
```

```
His Pro Ala Ser Thr Thr His Gln Gln Leu Ser Asp Glu Glu Gln Leu
385                 390                 395                 400

Ser Ala Gly Val Thr Pro Asp Leu Val Arg Val Ser Val Gly Ile Glu
                405                 410                 415

His Ile Asp Asp Ile Lys Glu Asp Phe Gln Gln Ala Phe Gly Gln Val
            420                 425                 430

Lys Ile

<210> SEQ ID NO 40
<211> LENGTH: 403
<212> TYPE: PRT
<213> ORGANISM: Pseudomonas aeruginosa

<400> SEQUENCE: 40

Met Thr Gln Asp Trp Asp Ala Gly Arg Leu Asp Ser Asp Leu Glu Gly
1               5                   10                  15

Ala Ala Phe Asp Thr Leu Ala Val Arg Ala Gly Gln Arg Arg Thr Pro
                20                  25                  30

Glu Gly Glu His Gly Glu Ala Leu Phe Thr Thr Ser Ser Tyr Val Phe
            35                  40                  45

Arg Thr Ala Ala Asp Ala Ala Ala Arg Phe Ala Gly Glu Val Pro Gly
        50                  55                  60

Asn Val Tyr Ser Arg Tyr Thr Asn Pro Thr Val Arg Thr Phe Glu Glu
65                  70                  75                  80

Arg Ile Ala Ala Leu Glu Gly Ala Glu Gln Ala Val Ala Thr Ala Ser
                85                  90                  95

Gly Met Ser Ala Ile Leu Ala Leu Val Met Ser Leu Cys Ser Ser Gly
                100                 105                 110

Asp His Val Leu Val Ser Arg Ser Val Phe Gly Ser Thr Ile Ser Leu
            115                 120                 125

Phe Asp Lys Tyr Phe Lys Arg Phe Gly Ile Gln Val Asp Tyr Pro Pro
130                 135                 140

Leu Ser Asp Leu Ala Ala Trp Glu Ala Ala Cys Lys Pro Asn Thr Lys
145                 150                 155                 160

Leu Phe Phe Val Glu Ser Pro Ser Asn Pro Leu Ala Glu Leu Val Asp
                165                 170                 175

Ile Ala Ala Leu Ala Glu Ile Ala His Ala Lys Gly Ala Leu Leu Ala
            180                 185                 190

Val Asp Asn Cys Phe Cys Thr Pro Ala Leu Gln Gln Pro Leu Lys Leu
        195                 200                 205

Gly Ala Asp Val Val Ile His Ser Ala Thr Lys Tyr Ile Asp Gly Gln
210                 215                 220

Gly Arg Gly Met Gly Gly Val Val Ala Gly Arg Gly Glu Gln Met Lys
225                 230                 235                 240

Glu Val Val Gly Phe Leu Arg Thr Ala Gly Pro Thr Leu Ser Pro Phe
                245                 250                 255

Asn Ala Trp Leu Phe Leu Lys Gly Leu Glu Thr Leu Arg Ile Arg Met
            260                 265                 270

Gln Ala His Ser Ala Ser Ala Leu Ala Leu Ala Glu Trp Leu Glu Arg
        275                 280                 285

Gln Pro Gly Ile Glu Arg Val Tyr Tyr Ala Gly Leu Pro Ser His Pro
290                 295                 300

Gln His Glu Leu Ala Arg Arg Gln Gln Ser Gly Phe Gly Ala Val Val
305                 310                 315                 320
```

```
Ser Phe Asp Val Lys Gly Gly Arg Asp Ala Ala Trp Arg Phe Ile Asp
                325                 330                 335

Ala Thr Arg Met Val Ser Ile Thr Thr Asn Leu Gly Asp Thr Lys Thr
            340                 345                 350

Thr Ile Ala His Pro Ala Thr Thr Ser His Gly Arg Leu Ser Pro Glu
        355                 360                 365

Asp Arg Ala Arg Ala Gly Ile Gly Asp Ser Leu Ile Arg Val Ala Val
    370                 375                 380

Gly Leu Glu Asp Leu Asp Asp Leu Lys Ala Asp Met Ala Arg Gly Leu
385                 390                 395                 400

Ala Ala Leu

<210> SEQ ID NO 41
<211> LENGTH: 379
<212> TYPE: PRT
<213> ORGANISM: Leptospira meyeri

<400> SEQUENCE: 41

Met Pro Thr Ser Glu Gln Asn Glu Phe Ser His Gly Ser Val Gly Val
1               5                   10                  15

Val Tyr Thr Gln Ser Ile Arg Phe Glu Ser Leu Thr Leu Glu Gly Gly
            20                  25                  30

Glu Thr Ile Thr Pro Leu Glu Ile Ala Tyr Glu Thr Tyr Gly Thr Leu
        35                  40                  45

Asn Glu Lys Lys Asp Asn Ala Ile Leu Val Cys His Ala Leu Ser Gly
    50                  55                  60

Asp Ala His Ala Ala Gly Phe His Glu Gly Asp Lys Arg Pro Gly Trp
65                  70                  75                  80

Trp Asp Tyr Tyr Ile Gly Pro Gly Lys Ser Phe Asp Thr Asn Arg Tyr
                85                  90                  95

Phe Ile Ile Ser Ser Asn Val Ile Gly Gly Cys Lys Gly Ser Ser Gly
            100                 105                 110

Pro Leu Thr Ile Asn Gly Lys Asn Gly Lys Pro Phe Gln Ser Thr Phe
        115                 120                 125

Pro Phe Val Ser Ile Gly Asp Met Val Asn Ala Gln Glu Lys Leu Ile
    130                 135                 140

Ser His Phe Gly Ile His Lys Leu Phe Ala Val Ala Gly Gly Ser Met
145                 150                 155                 160

Gly Gly Met Gln Ala Leu Gln Trp Ser Val Ala Tyr Pro Asp Arg Leu
                165                 170                 175

Lys Asn Cys Ile Val Met Ala Ser Ser Glu His Ser Ala Gln Gln
            180                 185                 190

Ile Ala Phe Asn Glu Val Gly Arg Gln Ala Ile Leu Ser Asp Pro Asn
        195                 200                 205

Trp Asn Gln Gly Leu Tyr Thr Gln Glu Asn Arg Pro Ser Lys Gly Leu
    210                 215                 220

Ala Leu Ala Arg Met Met Gly His Ile Thr Tyr Leu Ser Asp Glu Met
225                 230                 235                 240

Met Arg Glu Lys Phe Gly Arg Lys Pro Pro Lys Gly Asn Ile Gln Ser
                245                 250                 255

Thr Asp Phe Ala Val Gly Ser Tyr Leu Ile Tyr Gln Gly Glu Ser Phe
            260                 265                 270

Val Asp Arg Phe Asp Ala Asn Ser Tyr Ile Tyr Val Thr Lys Ala Leu
        275                 280                 285
```

```
Asp His Phe Ser Leu Gly Thr Gly Lys Glu Leu Thr Lys Val Leu Ala
        290                 295                 300

Lys Val Arg Cys Arg Phe Leu Val Val Ala Tyr Thr Ser Asp Trp Leu
305                 310                 315                 320

Tyr Pro Pro Tyr Gln Ser Glu Glu Ile Val Lys Ser Leu Glu Val Asn
                    325                 330                 335

Ala Val Pro Val Ser Phe Val Glu Leu Asn Asn Pro Ala Gly Arg His
                340                 345                 350

Asp Ser Phe Leu Leu Pro Ser Glu Gln Gln Asp Ser Ile Leu Arg Asp
            355                 360                 365

Phe Leu Ser Ser Thr Asp Glu Gly Val Phe Leu
        370                 375

<210> SEQ ID NO 42
<211> LENGTH: 378
<212> TYPE: PRT
<213> ORGANISM: Chloroflexus aurantiacus

<400> SEQUENCE: 42

Met Glu Ala Ile Val Gln Ala Pro Thr Pro Glu Gly Val Gly Ile Val
1               5                   10                  15

Arg Thr Gln Arg Met His Trp Thr Thr Pro Leu Thr Leu Thr Ser Gly
                20                  25                  30

Ala Thr Leu Gly Pro Ile Thr Leu Ala Tyr Glu Thr Tyr Gly Glu Leu
            35                  40                  45

Ala Pro Asp Arg Ser Asn Ala Ile Leu Ile Leu His Ala Leu Ser Gly
        50                  55                  60

Asp Ala His Ala Ala Gly Phe His Ser Pro Thr Asp Arg Lys Pro Gly
65                  70                  75                  80

Trp Trp Asp Ala Met Ile Gly Pro Gly Arg Pro Phe Asp Thr Asn Arg
                85                  90                  95

Tyr Phe Val Ile Cys Ser Asn Val Ile Gly Gly Cys Arg Gly Ser Thr
                100                 105                 110

Gly Pro Ser Ser Pro His Pro Ser Asp Gly Arg Pro Tyr Gly Ser Arg
            115                 120                 125

Phe Pro Leu Ile Thr Ile Glu Asp Met Val His Ala Gln Gln Arg Leu
        130                 135                 140

Ile Asp Ala Leu Gly Ile Asp Thr Leu Leu Ala Val Ala Gly Gly Ser
145                 150                 155                 160

Met Gly Gly Phe Gln Ala Leu Ala Trp Thr Val Glu Tyr Pro Gln Arg
                165                 170                 175

Val Arg Gly Ala Ile Leu Leu Ala Thr Ser Ala Arg Ser Ser Pro Gln
            180                 185                 190

Thr Val Ala Trp Asn Tyr Ile Gly Arg Arg Ala Ile Met Ala Asp Pro
        195                 200                 205

Arg Trp Arg Gly Gly Asp Tyr Tyr Asp Ser Asp Ala Pro Arg Asp Gly
210                 215                 220

Leu Ala Val Ala Arg Met Leu Gly His Ile Thr Tyr Leu Cys Glu Glu
225                 230                 235                 240

Lys Leu Glu Gln Arg Phe Gly Arg Val Asp Gly Asp Ala Leu Asp
                245                 250                 255

Leu Gly Pro Arg Phe Ala Ile Glu His Tyr Leu Glu His Gln Ala Ala
            260                 265                 270

Arg Phe Asn Asp Arg Phe Asp Ala Asn Ser Tyr Leu Val Ile Thr Arg
        275                 280                 285
```

```
Ala Met Asp Asn Trp Asp Leu Thr Ala Arg Tyr Gly Ser Leu Thr Ala
        290                 295                 300

Ala Phe Asp Leu Thr Arg Ala Arg Phe Leu Ala Leu Ala Tyr Ser Ser
305                 310                 315                 320

Asp Trp Leu Tyr Pro Pro Ala Glu Thr Tyr Gln Met Ala Ala Ala
                325                 330                 335

Gln Ala Ala Gly Arg Ser Phe Thr Thr His Leu Ile Thr Thr Asp Ala
            340                 345                 350

Gly His Asp Ala Phe Leu Thr Asp Val Ala Ala Gln Ser Glu Leu Ile
        355                 360                 365

Arg Asp Phe Leu Asn Arg Leu Met Thr Glu
        370                 375

<210> SEQ ID NO 43
<211> LENGTH: 356
<212> TYPE: PRT
<213> ORGANISM: Nostoc punctiforme

<400> SEQUENCE: 43

Met Ile Tyr Ser Asp Phe Ile Ser Pro Gln Thr Gln Phe Tyr Gln Leu
1               5                   10                  15

Thr Val Pro Phe Gln Leu Glu Ser Gly Lys Val Leu Ile Gly Val Gln
            20                  25                  30

Val Ala Tyr Arg Ser Trp Gly Glu Leu Asn Ala Gln Gly Asp Asn Gly
        35                  40                  45

Val Leu Ile Cys His Ala Leu Thr Gly Ser Ala Asp Ala Asp Asp Trp
    50                  55                  60

Trp Glu Pro Leu Phe Gly Ser Gly Lys Ala Phe Asn Pro Asp Arg Asp
65                  70                  75                  80

Phe Ile Val Cys Ser Asn Ile Leu Gly Ser Cys Tyr Gly Thr Thr Gly
                85                  90                  95

Pro Thr Thr Ile Asn Pro Thr Thr Arg Lys Pro Tyr Gly Val Ser Phe
            100                 105                 110

Pro Lys Ile Thr Ile Arg Asp Met Val Arg Leu Gln Ala Val Leu Leu
        115                 120                 125

Glu Tyr Leu Gly Val Gln Ser Leu Arg Phe Val Ile Gly Gly Ser Leu
    130                 135                 140

Gly Gly Met Gln Ser Leu Glu Trp Ala Leu Leu Tyr Pro Asp Lys Val
145                 150                 155                 160

Lys Ser Ile Ala Pro Ile Ala Val Ser Gly Arg His Ser Ala Trp Cys
                165                 170                 175

Ile Gly Leu Ser Glu Ala Gln Arg Gln Ala Ile Tyr Ala Asp Pro Asn
            180                 185                 190

Trp Gln Gly Gly Asn Tyr Thr Leu Asp Ala Pro Asn Gln Gly Leu
        195                 200                 205

Ala Val Ala Arg Met Met Ala Met Ser Thr Tyr Arg Ser Trp Asp Ser
    210                 215                 220

Phe Thr Thr Arg Phe Gly Arg Gln Tyr Asp Pro Ser Glu Lys Phe Ala
225                 230                 235                 240

Ile Ala Ser Tyr Leu Gln His Gln Gly Gln Lys Leu Thr Glu Arg Phe
                245                 250                 255

Asp Ala Asn Thr Tyr Ile Ile Leu Thr His Ala Met Asp Gly His Asp
            260                 265                 270

Ile Ala Arg Asp Arg Thr Ala Pro Asn Leu Ser Asp Tyr Glu Ser Val
        275                 280                 285
```

```
Leu Gly Ser Ile Gln Gln Pro Thr Leu Val Val Ala Ile Asp Ser Asp
        290                 295                 300

Ile Leu Tyr Pro Pro Val Glu Gln Gln Glu Leu Ala Asn Leu Ile Pro
305                 310                 315                 320

Asn Ala Gln Leu Ser Trp Leu Lys Ser Thr His Gly His Asp Ala Phe
                325                 330                 335

Leu Ile Asp Met Ala Ala Leu Asn Glu Ile Ile Gln Gln Asn His Glu
            340                 345                 350

Phe Val Leu Phe
            355

<210> SEQ ID NO 44
<211> LENGTH: 1278
<212> TYPE: DNA
<213> ORGANISM: Pseudomonas aeruginosa

<400> SEQUENCE: 44
atgaaactgg aaaccctggc cgtccacgcc ggctacagcc ctgacccgac cacccgcgcg    60
gtggcggtgc cgatctacca gaccacctcc tacgccttcg acgacaccca gcatggcgcc   120
gacctgttcg acctgaaggt accgggcaac atctacacac ggatcatgaa ccccaccaac   180
gacgtactgg aacagcgcgt cgcggcgctg aaggcggggt cggggcgct ggcggtggcc    240 tcggggatgg cggccatcac ctacgcgatc cagaccgtcg ccgaggccgg cgacaacatc   300
gtctcggtgg ccaagctcta cggcggcacc tacaacctgc tggcccacac cctgccacgc   360
atcggcatcc aggcgcgctt cgccgcccac gacgacgtcg ccgccctgga agcgctgatc   420
gacgagcgga ccaaggccgt gttctgcgaa accatcggca cccggcgggg caacatcatc   480
gacctgcagg cactggccga cgccgctcac cgccacggcg tgccactgat cgtcgacaac   540
acggtagcca ccccggtgct ctgccggccg ttcgagcacg cgccgacat cgtcgtgcac    600 tcgctgacca gtacatgggg cggccacggc ccagcatcg gcgggatcgt ggtcgactcc   660
ggcaaattcg actgggcggc gaacaagtcg cgcttcccgc tgctgaacac gcccgatccg   720
tcctaccacg cgtcaccta caccgaggcc ttcggacccg ccgccttcat cggccgctgc    780
cgggtggtac cgctgcgcaa catgggcgcg cgctctcgc cgttcaacgc cttcctcatc    840
ctccaaggcc tggagaccct ggcgctgcgc atggagcgcc actgcgacaa cgccctcgcc   900
gtggcccgct acctgcagca gcatccgcag gtggcctggg tgaaatacgc cggcctcgcc   960
gacaaccccg agcacgccct ggccggcgc tacctggggg ccgcccggc ggcgatcctg    1020 tctttcggca tccagggcgg cagcgccgcc ggcgcgcgct tcatcgacgc cttgaagctg   1080
gtggtgcggc tggtcaacat cggcgacgcc aagtccctgg cctgccaccc ggcgagcacc   1140
acccaccgcc agttgaacgc ggaggaactg gcccgcgccg agtctccga cgacatggtg    1200 cggctgtcga tcggcatcga gcacatcgac gacatcctcg ccgacctcga ccaggccctg   1260
gccgccgccg cacgctga                                                 1278

<210> SEQ ID NO 45
<211> LENGTH: 1329
<212> TYPE: DNA
<213> ORGANISM: Leptospira meyeri

<400> SEQUENCE: 45
atggtaggac atcgggggga atctatgcca cgtaattta aaccagaaac catcgcactc     60
cacggaggac aggaaccgga tccgaccacc acatcgagag ctgtgccact gtaccaaacc   120
acatcctatg tatttaaaga tacagaccat gctgcccgac ttttcggtct gcaagagttt   180
```

```
ggaaatatct atacaaggct tatgaatcca accacagatg ttttagaaaa acgtgtggct    240
gctttagaag gtggtgtcgc tgcgcttgca actgcatctg acaaagtgc tgaaatgtta    300 gcactcctca acatcgtgga agcaggacaa gaaattgttg cgtcttcttc tttatatggt    360
ggaacctaca acctactcca ttatacattc cctaaactcg gaatcaaagt gcactttgta    420
gaccagtcag atcctgaaaa ctttcgtaaa gcatcgaatg ataaaacgag agcattttat    480
gcagaaacgt taggaaatcc aaaattagat accttagaca ttgcagcggt tagcaaagta    540
gctaaggaag taggtgttcc gcttgtgatt gataacacaa tgccttctcc ttatttagtg    600
aacccactca acatggtgc agacatagtg gtccactctc tcactaaatt tttaggcggt    660
catggaactt ccattggtgg aatcatcatc gatggtggaa gtttcaattg ggggaatgga    720
aaatttaaga atttcacaga gccagatccg tcataccatg gactaaagtt ttgggaagtc    780
tttggaaagt tcgaaccttt cggcggggtg aacattgctt ttattttgaa agctcgagta    840
caaggtcttc gcgatcttgg cccagcgatt tctcctttca atgcttggca aattttacaa    900
ggtgtggaaa ctcttccact tcgtatggaa cgacactcag gtaatgctct caaagttgcc    960 gagttttac aaaaacatcc aaagattgaa tgggtcaatt acccaggcct ttcaactgac    1020
aaaaactatg ccacagccaa aaaataccat gaacgtggac ttttttggtgc aatcgtagga    1080 tttgaaatca aggtggcgt agaaaaagcc aaaaaattta ttgatggatt ggaacttttt    1140
agtcttcttg ctaacattgg tgatgcgaag tctcttgcca ttcacccggc ttccacaact    1200
caccaacagc tgactggtcc ggaacaaatt tctgcgggag ttaccctgg atttgttcgt    1260 ttgagtgtcg gtcttgaaaa cattgatgac attctggtag acttggaaga ggcattaaaa    1320
aatatctga                                                           1329
```

<210> SEQ ID NO 46
<211> LENGTH: 1455
<212> TYPE: DNA
<213> ORGANISM: Chloroflexus aurantiacus

<400> SEQUENCE: 46

```
atgcgtcgcc gcatacgaac ggtgctaagt ccggcagagg tgttctggaa gatgagcgac     60
gtggaagaac ggcttagtgc aacgatttca cgccctcatc gcacgttgag ggcgttttg    120 ttgcctgcaa tctggcttat ctgttttgag gaggttgtta tgtctgatgc tccgcgcttc    180
accggttttg aaactctcgc cctgcatgcc ggccaaaccc ccgatccgac cactgggtcg    240
cgagctgttc ctatctacgc caccacatcc tatcaattca agacacaga ccatgcagca    300 cgcctgttca atctgcaaga gtttggtaat atctacactc gcattatgaa tccgaccacc    360
gatgtctttg aacagcggat ggcggcactg gagggcggag taggtgcgct ggcgctggca    420
tcggggcagg ccgctgaaac gctggctatt ctcaacctgg ccggaagtgg cgacaatatc    480
gtcgcatcct ctgacctgta tggcggcacc tacaacctct ccgtcatac attaccaaag    540 ttaggcatta cgactcgctt tgttgatgcc cgtgattacg atggctttgc cgctgcgatt    600
gatgggcgta ccaaagcctt cttcctcgaa ttagtcggca atccacggct tgatgtgctc    660
gatctggagc gcattgccgc aattgcgcat gcgcagggtg tgccggtcat cgtcgatgcg    720
accacggtca caccgtacct gtggcaaccg atccagcacg gcgccgatat tgtgattcac    780
tcggcaacca agtacattgg tggtcatggc acggctatcg gaggcatcat tgttgacagt    840
ggtaagtttg attgggcagc cagtggccgt ttttcccgaat ttaccaatcc cgatccgagc    900
tatcacggcc tgatctatac ccaggctttc ggcaacctgg cgtacattat caaggcacga    960
```

-continued

```
gtgcaagggc tacgcgacat tggggctgcg cttagcccat ttaacagctt cctgttcctg      1020
caagggctgg agacgttgcc actccggatg gaacgacaca gcaagaatgc gctggcagtg      1080
gcccgttatc tgagtgagca tcccaaagtg gcgtgggtca actacccgg tcttcccagc       1140 catccaagct atgccctggc tcagaaatat ctgccgcgtg ggcagagtgg gattgttggc      1200
ttcggcctga agggtgggcg tgccgccgga cgtaccttca ttgagcggtt acggctcttc      1260
tcgcacctcg ccaatattgg cgatgccaag agccttgcga tccatccggc aaccaccacc      1320
cacagccagt tgacgccgga agaacaattg ctgaccggcg tgaccgacga ttatgtccgg      1380
ctctcgattg gcctggagac gattgacgat attctggccg atcttgatca tgccctggca      1440
ggaaccccat catag                                                        1455

<210> SEQ ID NO 47
<211> LENGTH: 1305
<212> TYPE: DNA
<213> ORGANISM: Nostoc punctiforme

<400> SEQUENCE: 47
atgtctgaac aatatcgttt tgaaactctg caagttcatg ctggacaaga gccggctcct        60
ggaaataatg cccgtgctgt accaatttac caaacgactt cctacgtttt tgacgacacc       120
gaacacggag cgcggttatt tgctctccag gaatttggca acatttacac ccgaatcatg       180
aacccgacga cggatgtatt tgaaaagcgg attgctgcac tagaaggggg tgtagcagca       240
ttagcaaccg ctagtggtca ggcggcgcaa ttcttggcaa tcagtaccat cgctcaggct       300
ggggataata tcgtttccac tagttttttg tatggggaa catataacca gtttaaagtc        360
tcactaccac gtttagggat taacgtcaag tttgtcgagg gagacgatcc agaaagtttc       420
cgtcaggcga tcgacgctcg caccaaagcg ttatacgttg aaaccattgg caatcctcag       480
tataacattc ctgactttgc cgctttagct cacattgccc acgaaaacgg catacctta        540 attgtggata ataccttgg tgctggtgga tatttagctc gacccattga acatggtgca        600
gacattgtag ttgaatctgc aactaaatgg attggtgggc atggtacttc cattggtggc       660
gtaatagtcg attcgggtaa atttgactgg ggtaacggca aatttccact atttactgag       720
ccagcacccg gctatcatgg gctgaatttc caagaagtgt ttgggcctag cggttccttt       780
ggcaacattg cttttattat ccgcgctaga gtcgaggggt tacgggattt tggcccatct       840
ttgagtccat ttaacgcctt tctttttactg caaggattag agactctctc tttgcgtgta       900
gatcgtcatg tcagcaatgc cttagaattg gctcggtggt tagagcagca agagcaagta       960
ttatgggtta attatcccgg acttcctaat cactcatatc atgaacgagc gaaaaaatat      1020
ctccggcatg ggtttgggg agttttaaac tttggcatca aaggtggatt ggaggcaggt      1080 aaagcttta ttaatcatgt gaaattggca agtcatttag caaatgttgg tgatgctaaa      1140
accctcgtta ttcatcccgc ttccacaact catcaacagc taagtgatga agaacagctt      1200
tcagcaggtg taacgcccga tttagtgcgc gtatcagtgg gaattgaaca tatcgacgat      1260
attaaagagg attttcagca agcattcggg caagttaaga tttaa                      1305
```

COMPOSITIONS AND METHODS OF PRODUCING METHIONINE

CROSS REFERENCE TO RELATED APPLICATIONS

This application is the National Stage of International Application No. PCT/US2007/00914, filed Apr. 11, 2007.

REFERENCE TO SEQUENCE LISTING SUBMITTED ELECTRONICALLY VIA EFS-WEB

The content of the electronically submitted sequence listing (Name: 2511_0050000SEQIDLisitng_AmendUpdate.ascii.txt; Size: 64,460 bytes; and Date of Creation: Oct. 3, 2012) is incorporated by reference in its entirety.

FIELD

Disclosed are compositions, such as microorganisms, enzymes, and chemicals, as well as methods for using the same for producing methionine and related products.

BACKGROUND

Methionine is an essential amino acid in the animal diet. Methionine has been produced synthetically for an extensive period of time by various multi-step chemical synthesis employing acrolein, methyl mercaptan and cyanide as starting materials. There are two product forms: D,L methionine and its hydroxyanalog. D-methionine is converted into the required L-isomer in vivo, unlike all other amino acids. The market for feed-grade methionine has been reported to be improving due to increased demand in poultry and more recently swine feed supplementation. The ability of the leading methionine producers (Degussa AG, Adisseo, and Novus) to meet the market demand hinges on raw material supplies. The intermediates acrolein and methyl mercaptan must be converted into 3-methylthiopropionaldehyde (MMP) and further into methionine using hydrogen cyanide. All three producers have plans for expansion of their methionine production facilities and integration with raw material production as well (Chem. Marketing Reporter Apr. 7, 2003).

The biosynthetic pathways for methionine (a member of the aspartate family of amino acids) have been studied in a number of organisms and show similarities as well as differences. The first dedicated step, acylation of homoserine is catalyzed by homoserine acyltransferase, and is ubiquitous in all organisms despite differences in the transferred acyl group. The product of metA catalysis is either acetylhomoserine or succinylhomoserine. Acylhomoserine is then converted to homocysteine via a transsulfuration or a direct sulfhydrylation pathway. Both pathways have been reported to be present and functional in yeast, fungi, green plants and the bacterium *Corynebacterium glutamicum*. *E. coli* possesses only the transsulfuration pathway. The transsulfuration pathway goes through cystathionine as an intermediate and utilizes cysteine as a sulfur donor. The direct sulfhydrylation pathway involves the direct incorporation of sulfide to the acylhomoserine. The last step in the pathway involves the conversion of homocysteine to methionine catalyzed by an homocysteine methyltransferase, encoded by the metE or metH genes.

Other important amino acids, such as lysine, threonine, and tryptophan are produced via fermentation for use in animal feed. Therefore, these amino acids can be made using glucose and other renewable resources as starting materials. Unfortunately, the production of methionine via fermentation has not been as successful and the chemical synthesis of methionine is still used today. This is in part due to the lack of an efficient engineered biosynthetic pathway for methionine production, and a suitable production host.

The following disclosure provides an improved methionine biosynthetic pathway, as well as production host.

SUMMARY

The production of methionine and related products, such as S-adenosylmethionine (SAMe), by fermentation are described herein. Microorganisms that have been genetically engineered to include recombinant DNA molecules and produce methionine are also described.

A microorganism that includes an exogenous nucleic acid sequence encoding a peptide having direct sulfhydrylation activity (EC 2.5.1.49, EC 4.2.99-), and endogenous nucleic acid sequences encoding peptides having transsulfuration activity (EC 2.5.1.48 and 4.4.1.8) is described. This microorganism can produce methionine and related products. In some examples, the microorganism can have at least 0.1, 1, 2, 5, 10, 50, 75, 90, or at least 100 g/L extracellular concentration of methionine or SAMe.

In some examples, the presence of more than one methionine biosynthetic pathway allows the organism to produce more methionine than would be produced in the absence of the exogenous nucleic acid sequence encoding the peptide having direct sulfhydrylation activity.

In other examples, more than two methionine biosynthetic pathways can be active in the organism. In these examples one or more exogenous nucleic acid sequences encode for peptides having direct sulfhydrylation activity. One of these peptides can use O-succinylhomoserine as a substrate and another peptide can use O-acetylhomoserine as a substrate.

In some examples, the microorganisms engineered to make methionine and related products, such as SAMe, produce at least 10% of the methionine from transsulfuration biosynthetic pathway activity. In other examples they produce at least 20, 30, 40, or at least 50% of the product from the transsulfuration biosynthetic pathway activity.

In some examples, the microorganisms engineered to make methionine and related products, such as SAMe, produce at least 10% of the methionine from direct sulfhydrylation biosynthetic pathway activity. In other examples they produce at least 20, 30, 40, or at least 50% of the product from the direct sulfhydrylation biosynthetic pathway activity.

In some examples, the microorganism engineered to make methionine and related products additionally has been engineered to attenuate the activity of a peptide encoded by a gene such as metD, metK, meg thrB, serA or combinations thereof. In other examples, the microorganism is additionally engineered to over express one or more genes, such as the metA, metB, metC, metE, metY, metZ, metX, metH, cysPWUA, cysD, cysN, cysC, cysH, cysI, cysJ, cysG, csyK and cysM genes.

Methods of making methionine and SAMe are also provided. These methods include culturing the microorganism engineered to make methionine and related products and isolating the products. In some examples the microorganism can be *E. coli, Pseudomonas* sp., or *Corynebacterium glutamicum*.

Also described herein are novel nucleic acid sequences and their corresponding amino acid sequences (SEQ ID NOS: 1 and 2). These nucleic acid sequences, as well as fragments and variants of these nucleic acid sequences, are useful for producing peptides in recombinant microorganisms. The peptides are useful, inter alia, for producing methionine and SAMe. The peptides, variants thereof, and fragments thereof, are also useful for producing specific binding agents such as antibodies.

A method of improving sulfur assimilation by bypassing the phosphoadenylylsulfate (PAPS) intermediate is also disclosed. This method can be used with any microorganism used to produce methionine. The method is accomplished by introducing into a microorganism a recombinant nucleic acid sequence that allows for the over expression of one or more adenylyl sulfate reductases (EC 1.8.9.92 or 1.8.4.9). Over expression can be from introducing recombinant nucleic acid sequences altering or introducing new control elements, such as promoters or enhancers, that cause an increase in the production of endogenous adenylyl sulfate reductase or the recombinant nucleic acid sequence can encode adenylyl sulfate reductase.

These and other aspects of the disclosure are apparent from the following detailed description and illustrative examples.

SEQUENCE LISTING

Figure 1:
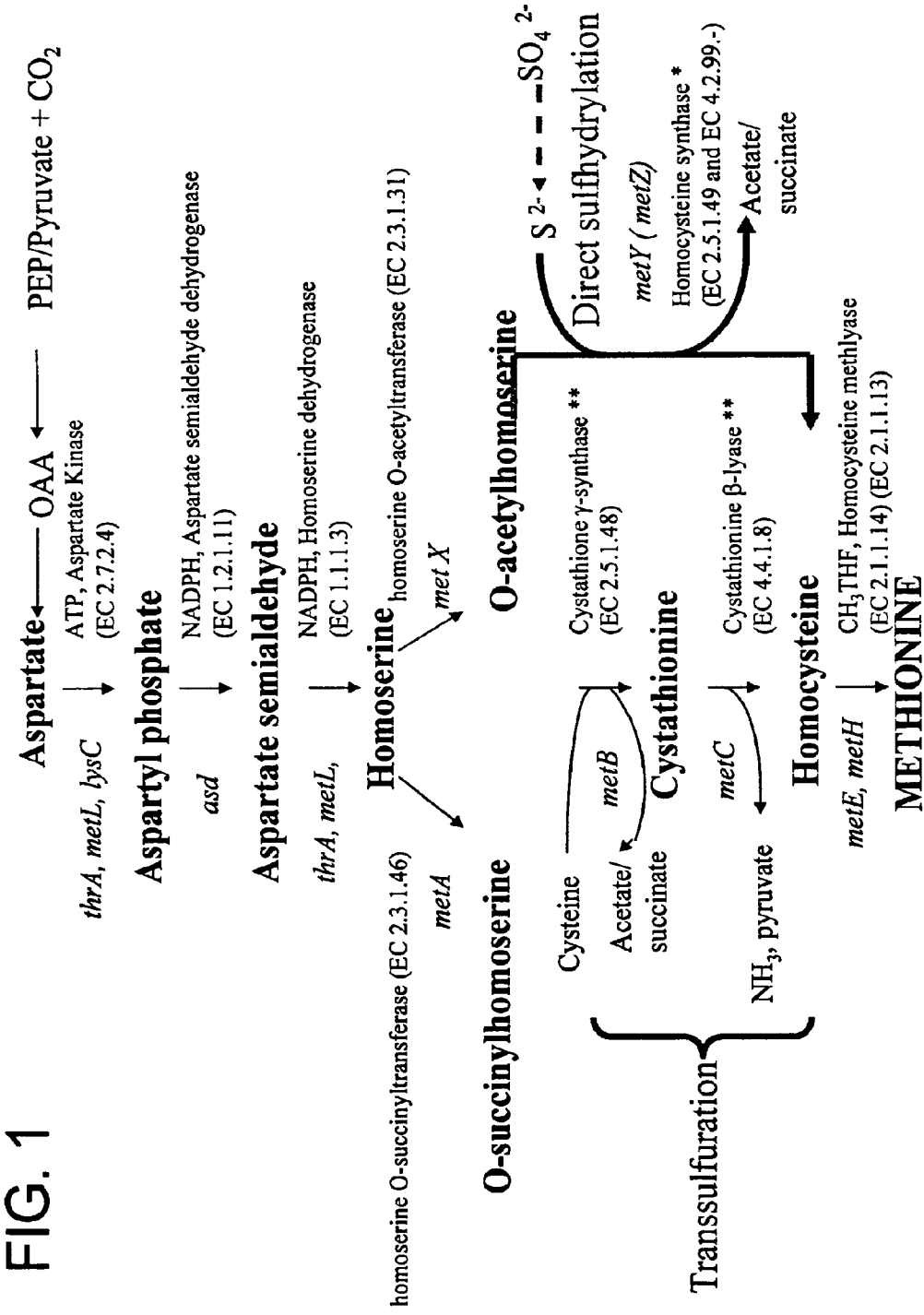
FIG. 1. is a diagram showing three general pathways used by various microorganisms to produce methionine. All of the pathways rely in part upon the use of aspartate as a precursor for methionine production. Aspartate is converted through multiple steps to homoserine, homoserine is converted to O-acetyl homoserine or O-succinyl homoserine by MetA or MetX. Some microorganisms, such as *E. coli* and *Pseudomonas* sp. utilize MetA polypeptides to make O-succinyl homoserine while other microorganisms such as *Corynebacterium* and *Leptospira* sp. use MetX to make O-acetyl homoserine. O-succinyl homoserine and O-acetyl homoserine can be then either directly converted to homocysteine through sulfhydrylation, or they can be converted to homocysteine through transsulfuration (both of which reactions are described in more detail herein). Enzymes associated with transsulfuration are identified with two asterisks (**), and enzymes associated with sulfhydrylation are identified with a single asterisk (*).

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood as included by any reference to the displayed strand.

SEQ ID NOS: 1-10 show nucleic acid sequences and corresponding amino acid sequences of various mutant metA genes derived from *E. coli*.

SEQ ID NOS: 11 through 34 show various primer sequences used in the Examples.

DETAILED DESCRIPTION

Abbreviations and Terms

The following explanations of terms and methods are provided to better describe the present disclosure and to guide those of ordinary skill in the art in the practice of the present disclosure. As used herein, "comprising" means "including"and the singular forms "a" or "an" or "the" include plural references unless the context clearly dictates otherwise. For example, reference to "comprising a cell"includes one or a plurality of such cells, and reference to "comprising the homocysteine synthase peptide" includes reference to one or more homocysteine synthase peptides and equivalents thereof known to those of ordinary skill in the art, and so forth. The term "or" refers to a single element of stated alternative elements or a combination of two or more elements, unless the context clearly indicates otherwise. For example, the phrase "homocysteine synthase activity or cystathionine γ-synthase activity" refers to homocysteine synthase activity, cystathionine γ-synthase activity, or a combination of both homocysteine synthase activity, and cystathionine γ-synthase activity.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

Accession Numbers: The accession numbers throughout this description are derived from the NCBI database (National Center for Biotechnology Information) maintained by the National Institute of Health, U.S.A. The accession numbers are as provided in the database on Feb. 20, 2007.

Enzyme Classification numbers (EC.): The EC numbers provided throughout this description are derived from the KEGG Ligand database, maintained by the Kyoto Encyclopedia of Genes and Genomics, sponsored in part by the University of Tokyo. The EC numbers are as provided in the database on Feb. 20, 2007.

Attenuate: To lessen the impact, activity or strength of something. In one example, the sensitivity of a particular enzyme to feedback inhibition or inhibition caused by a composition that is not a product or a reactant (non-pathway specific feedback) is lessened such that the enzyme activity is not impacted by the presence of a compound. For example, the metA gene and its corresponding amino acid sequence (such as the exemplary sequences provided inSEQ ID NOS: 2) show several mutations that attenuate its feedback inhibition sensitivity. The attenuation of MetA sensitivity is described in more detail in Example 3.B. In another example, an enzyme that is less active can be referred to as attenuated.

cDNA (complementary DNA): A piece of DNA lacking internal, non-coding segments (introns) and regulatory sequences which determine transcription. cDNA can be synthesized by reverse transcription from messenger RNA extracted from cells.

Deletion: The removal of one or more nucleotides from a nucleic acid molecule or one or more amino acids from a protein, the regions on either side being joined together.

Detectable: Capable of having an existence or presence ascertained. For example, production of a product from a reactant, for example, the production of O-succinylhomoserine or homocysteine, is detectable if the signal generated from the product or the reactant, is strong enough to be measured.

Direct sulfhydrylation activity: the ability to react OSHS or OAHS directly with $S^{2-}$ to produce homocysteine. Peptides having this activity include for example, homocysteine synthases (EC 4.2.99.-, EC 2.5.1.49) which are encoded by genes such as metZ and metY.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a peptide. The term codon is also used for the corresponding (and complementary) sequences of three nucleotides in the mRNA into which the DNA sequence is transcribed.

Endogenous: As used herein with reference to a nucleic acid molecule and a particular cell or microorganism refers to a nucleic acid sequence or peptide that is in the cell and was not placed in the cell using recombinant engineering techniques. For example, a gene that was in the cell when the cell was originally isolated from nature. A gene is still considered endogenous if the control sequences, such as a promoter or enhancer sequences that activate transcription or translation have been altered through recombinant techniques.

Exogenous: As used herein with reference to a nucleic acid molecule and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type.

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Functional Deletion: A mutation, partial or complete deletion, insertion, or other variation made to a gene sequence which reduces or inhibits production of the gene product, or renders the gene product non-functional. For example, functional deletion of metJ in *E. coli* reduces the repression of the methionine biosynthetic pathway. In another example, functional deletion of thrB in *E. coli* reduces the use of homoserine in the threonine biosynthetic pathway. In some instances a functional deletion is described as a knock out mutation.

Isolated: An "isolated" biological component (such as a nucleic acid molecule, protein, or cell) has been substantially separated or purified away from other biological components in which the component naturally occurs, such as other chromosomal and extrachromosomal DNA and RNA, and proteins. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

In one example, isolated refers to a naturally-occurring nucleic acid molecule that is not immediately contiguous with both of the sequences with which it is immediately contiguous (one on the 5' end and one on the 3' end) in the naturally-occurring genome of the organism from which it is derived.

Nucleic acid molecule: Encompasses both RNA and DNA molecules including, without limitation, cDNA, genomic DNA, and mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecule can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus placing genes in close proximity, for example in a plasmid vector, under the transcriptional regulation of a single promoter, constitutes a synthetic operon.

ORF (open reading frame): A series of nucleotide triplets (codons) coding for peptides, polypeptides or amino acids without any termination codons. These sequences are usually translatable into a peptide.

Purified: The term purified does not require absolute purity; rather, it is intended as a relative term. Thus, for example, a purified peptide preparation, such as a succinyl-CoA homoserine acyltransferase, or a homocysteine synthase preparation, is one in which the peptide is more concentrated than the peptide is in its environment within a cell. For example, a purified peptide is one that is substantially separated from cellular components (nucleic acids, lipids, carbohydrates, and other peptides) that may accompany it. In another example, a purified peptide preparation is one in which the peptide is substantially-free from contaminants, such as those that might be present following chemical synthesis of the peptide.

In one example, a peptide is purified when at least about 50% by weight of a sample is composed of the peptide, for example when at least about 60%, 70%, 80%, 85%, 90%, 92%, 95%, 98%, or 99% or more of a sample is composed of the peptide. Examples of methods that can be used to purify a peptide, include, but are not limited to the methods disclosed in Sambrook et al. (*Molecular Cloning: A Laboratory Manual*, Cold Spring Harbor, New York, 1989, Ch. 17). Protein purity can be determined by, for example, polyacrylamide gel electrophoresis of a protein sample, followed by visualization of a single peptide band upon staining the polyacrylamide gel; high-pressure liquid chromatography; sequencing; or other conventional methods.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q −1 -r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, at least 80%, at least 85%, at least 90%, at least 95%, at least 97%, or at least 99% sequence identity to the subject sequence (i.e. sequence identified by accession number or the like), while retaining the activity of the subject sequence. In some examples, the subject sequence will have greater activity than that of the native sequence and in yet other examples it will be less active.

When aligning short peptides (fewer than approximately 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 60%, 70%, 75%, 80%, 85%, 90%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity to a subject sequence (sequences identified by accession number or the like).

One of skill in the art will appreciate that these sequence identity ranges are provided for guidance only; it is possible that strongly significant homologs could be obtained that fall outside the ranges provided.

Transformed cell: A cell into which a nucleic acid molecule has been introduced, such as a succinylCoA homoserine acyltransferase, or a homocysteine synthase nucleic acid molecule, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration.

Transsulfuration activity: An activity that produces methionine or SAMe via the intermediate, cystathionine. Peptides having this activity include cystathionine γ synthase (EC 2.5.1.48) and cystathionine β lyase (EC 4.4.1.8), these peptides are encoded by the genes metB and metC, respectively. Any combination of cystathionine γ synthase (EC 4.2.99.9) and cystathionine β lyase (EC 4.4.1.8) peptides can be used to allow a microorganism to possess transsulfuration activity.

Under conditions that permit product production: Any fermentation conditions that allow a microorganism to produce a desired product, such as methionine or SAMe. Conditions usually include temperature, aeration, and medium. The medium can be a broth or a gel. Generally, the medium includes a carbon source such as glucose, fructose, cellulose, or the like that can be metabolized by the microorganism directly, or enzymes can be used in the medium to facilitate metabolizing the carbon source. To determine if culture conditions permit product production, the microorganism can be cultured for 24, 36, or 48 hours and a sample can be taken. The cells in the sample can be then tested for the presence of the desired product. For example when testing for the presence of methionine or SAMe the assays provided in the Examples section may be used.

Vector: A nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art.

DETAILED DESCRIPTION

I. Methionine Production Pathways

As shown in FIG. 1, many biosynthetic pathways can be used to produce methionine or its intermediates such as aspartyl phosphate, aspartate semialdehyde homoserine, O-succinylhomoserine (OSHS), O-acetylhomoserine (OAHS), cystathionine, homocysteine, methionine, and S-adenosyl methionine (SAMe). For the purposes of this disclosure an intermediate can be referred to as a reactant or a product, depending upon context. For example, when discussing the conversion of aspartate to aspartyl phosphate using an aspartate kinase, the aspartate is the reactant and the aspartyl phosphate is the product. Similarly, when the description describes the conversion of aspartyl phosphate to aspartate semialdehyde using an aspatate semialdehyde dehydrogenase, the aspartyl phosphate is the reactant and the aspartate semialdehyde is the product. One of ordinary skill in the art will appreciate that FIG. 1 shows many biosynthetic pathways because within each enzyme class provided there are many enzymes that can be used to convert a reactant to a product and, therefore, make a pathway. Moreover, these reactions can be carried out in vivo, in vitro, or through a combination of in vivo reactions and in vitro reactions, such as in vitro reactions that include non-enzymatic chemical reactions.

The host microorganism can also be provided intermediates in the pathway by including the intermediates in the fermentation feedstock. Thus, if the biosynthetic pathway is producing less than a desired amount of a given intermediate, that intermediate can be added to the feedstock. This can be done in either a continuous fermentation setting or in a batch fermentation setting.

Those of ordinary skill in the art will recognize that a production host can use carbon sources other than glucose. Alternative carbons sources include for example, sucrose, fructose, cellulose, hemicellulose, starch, or glycerol. When alternative carbon sources are used it may be necessary to include enzymes that will modify the carbon source in the fermentation media.

A. Glucose to Aspartate

Microorganisms generally produce aspartate from glucose. One of ordinary skill in the art will appreciate that there are many methods of increasing the aspartate concentration in production strains. For example, increasing the expression of the enzymes pyruvate carboxylase and phosphoenolpyruvate carboxylase, altering the glyoxylate shunt or eliminating the consumption of pyruvate into other products such as acetate or ethanol.

Alternatively, aspartate can be included in the fermentation feedstock, taken up by the microorganism, and used as a reactant in the methionine biosynthetic pathway.

Aspartate also serves as an intermediate in the lysine, threonine, and asparagine biosynthetic pathways. Therefore, it may be desirable to attenuate or remove (knockout) these pathways, thus allowing more aspartate to be used in the methionine production pathway.

B. Aspartate to Aspartyl Phosphate

Production hosts can be engineered using known polypeptides to produce aspartyl phosphate, or to overproduce aspartyl phosphate. For example, the feed back resistant aspartate kinase described in WO04069996A2 can be used to replace an endogenous aspartate kinase or in addition to an endogenous aspartate kinase.

As used herein, aspartate kinase includes peptides in enzyme classification number (EC) 2.7.2.4, as well as any other peptide capable of catalyzing the conversion of aspartate to aspartyl phosphate. Additionally, one of ordinary skill in the art will appreciate that some aspartate kinase peptides will catalyse other reactions as well, for example some aspartate kinase peptides will accept other substrates in addition to aspartate. Such non-specific aspartate kinase peptides are, therefore, also included. Aspartate kinase sequences are publicly available. For example, GenBank Accession Nos: NZ_AAVY01000022, NC_006958, and NZ_AAWW01000055, disclose aspartate kinase nucleic acid sequences and GenBank Accession Nos: NP_418448, NP_599504 and ZP_01638096 disclose aspartate kinase peptide sequences. Assays for characterizing the aspartate kinase activity of a particular peptide are well known in the art. For example, the assay described by Cohen, G N, Methods in Enzymology, 113:596:600, 1985, can be used to characterize the activity of a specific peptide.

C. Aspartyl Phosphate to Aspartate Semialdehyde

Production hosts can be engineered using known polypeptides to produce aspartate semialdehyde, or to overproduce aspartate semialdehyde. One method of increasing the production of products in the methionine biosynthetic pathway is through over-expression or the expression of a more active form of aspartate semialdehyde dehydrogenase.

As used herein, aspartate semialdehyde dehydrogenase includes aspartate semialdehyde dehydrogenase peptides (EC 1.2.1.11), as well as any other peptide capable of catalyzing the conversion of aspartyl phosphate to aspartate semialdehyde. Additionally, one of ordinary skill in the art will appreciate that some aspartate semialdehyde dehydrogenase peptides will catalyze other reactions as well. For example, some aspartate semialdehyde dehydrogenase peptides will accept other substrates in addition to aspartyl phosphate, and therefore, such non-specific aspartate semialdehyde dehydrogenase peptides are also included. Aspartate semialdehyde dehydrogenase sequences are publicly available. For example, GenBank Accession Nos: NC_006958, NZ_AAVY01000015 and NZ_AAWW01000010 disclose aspartate semialdehyde dehydrogenase nucleic acid sequences and GenBank Accession Nos: NP_417891, NP_599505 and ZP_0164))72 disclose aspartate semialdehyde dehydrogenase peptide sequences. Assays for characterizing the aspartate semialdehyde dehydrogenase activity of a particular peptide are well known in the art. For example, the assay described by Cohen, G N., Methods in Enzymology, 113:600-602, 1985, can be used to characterize the activity of a specific peptide.

D. Aspartate Semialdehyde to Homoserine

Production hosts can be engineered using known polypeptides to produce homoserine, or to overproduce homoserine. One method of increasing the production of products in the methionine biosynthetic pathway is through over expression or the expression of a more active form of aspartate semialdehyde dehydrogenase.

As used herein, homoserine dehydrogenase includes homoserine dehydrogenase peptides (EC 1.1.1.3), as well as any other peptide capable of catalyzing the conversion of aspartate semialdehyde to homoserine. Additionally, one of ordinary skill in the art will appreciate that some homoserine dehydrogenase peptides will catalyze other reactions as well, for example some homoserine dehydrogenase peptides will accept other substrates in addition to aspartate semialdehyde. Such non-specific homoserine dehydrogenase peptides are, therefore, also included. Homoserine dehydrogenase peptide sequences are publicly available. For example, GenBank Accession Nos: NC_006958, NZ_AAVY01000013 and NZ_AAWW01000033 disclose homoserine dehydrogenase nucleic acid sequences and GenBank Accession Nos: NP_414543, ZP_01639819 and NP_600409 disclose homoserine dehydrogenase peptide sequences. Assays for characterizing the homoserine dehydrogenase activity of a particular peptide are well known in the art. For example, the assay described by Patte et.al., Biochem. Biophys. Acta 128: 426-439, 1966, can be used to characterize the activity of a specific peptide.

E. Homoserine to O-succinylhomoserine (OSHS)

Production hosts can be engineered using known polypeptides to produce O-succinylhomoserine (OSHS), or to overproduce OSHS. One method of increasing the production of products in the methionine biosynthetic pathway is through over expression or the expression of a more active form of homoserine O-succinyltransferase peptides, or using a feed back inhibition insensitive form of homoserine O-succinyltransferase peptides.

As used herein, succinylCoA homoserine acyltransferase, includes homoserine O-succinyltransferase peptides (EC 2.3.1.46), as well as any other peptide capable of catalyzing the conversion of homoserine to OSHS. Additionally, one of ordinary skill in the art will appreciate that some homoserine O-succinyltransferase peptides will catalyze other reactions as well, for example some succinylCoA -homoserine acyltransferase peptides will accept other substrates in addition to homoserine. Such non-specific succinylCoA -homoserine acyltransferase peptides are, therefore, also included. Homoserine O-succinyltransferase peptide sequences are publicly available. For example, GenBank Accession No: NZ_AAWW01000055 discloses a homoserine O-succinyltransferase nucleic acid sequence and GenBank Accession No: AAC76983 discloses a homoserine O-succinyltransferase peptide sequence. Assays for characterizing succinyl-CoA -homoserine acyltransferase activity are well known in the art. For example, the assay described by Lawrence, J. Bacteriol., 109:8-11, 1972, can be used to characterize the activity of a specific peptide. Genes encoding succinyl CoA -homoserine acyltransferase peptides are also referred to herein as metA.

F. Homoserine to O-acetylhomoserine (OAHS)

Production hosts can be engineered using known polypeptides to produce O-acetylhomoserine (OAHS), or to overproduce OAHS. One method of increasing the production of products in the methionine biosynthetic pathway is through over expression or the expression of a more active form of homoserine O-acetyltransferase peptides (EC 2.3.1.31).

As used herein, homoserine O-acetyltransferase, includes homoserine O-acetyltransferase peptides (EC 2.3.1.31), as well as any other peptide capable of catalyzing the conversion to OAHS. Additionally, one of ordinary skill in the art will appreciate that some homoserine O-acetyltransferase peptides will catalyze other reactions as well, for example some homoserine O-acetyltransferase peptides will accept other substrates in addition to homoserine. Such non-specific homoserine O-acetyltransferase peptides are, therefore, also included. Homoserine O-acetyltransferase peptide sequences are publicly available. For example, GenBank Accession Nos: Y10744 REGION: 2822 ... 3961, NZ_AAAH02000004 REGION: 166057 ... 167193 and NZ_AAAY02000081 REGION: complement(11535 ... 12605) disclose homoserine O-acetyltransferase nucleic acid sequences and GenBank Accession Nos: CAA71733, ZP_00766367 and ZP_00107218 disclose homoserine O-acetyltransferase peptide sequences. Assays for characterizing homoserine O-acetyltransferase activity are well known in the art. For example, the assay described by Lawrence, J. Bacteriol., 109:8-11, 1972, can be used to characterize the activity of a specific peptide. Genes encoding homoserine O-acetyltransferase peptides are also referred to herein as metX.

G. Sulfhydrylation

The production of homocysteine by direct sulfhydrylation is accomplished by homocysteine synthase enzymes, some of these enzymes utilize OSHS as a substrate, and some of utilize OAHS as a substrate. Additionally, some of the enzymes can utilize either OSHS or OAHS as substrates.

1. O-succinylhomoserine (OSHS) to Homocysteine

Production hosts can be engineered using known polypeptides to produce homocysteine, or to overproduce homocysteine. One method of increasing the production of products in the methionine biosynthetic pathway is through over expression or the expression of a more active form of homocysteine synthase peptides (EC 4.2.99.-).

As used herein, homocysteine synthase includes homocysteine synthase peptides (EC 4.2.99.-), as well as any other peptide capable of catalyzing the conversion of O-succinylhomoserine (OSHS) to homocysteine. The conversion of OSHS to homocysteine through reaction with sulfide is referred to herein as direct sulfhydrylation. Additionally, one of ordinary skill in the art will appreciate that some homocysteine synthase peptides will catalyze other reactions as well, for example some homocysteine synthase peptides will accept other substrates in addition to OSHS. Such non-specific homocysteine synthase peptides are, therefore, also included. Homocysteine synthase peptide sequences are publicly available. For example, GenBank Accession No: AE004091 discloses a homocysteine synthase (O-succynil-L-homoserine sulfhydrylase) nucleic acid sequences and GenBank Accession No: AAG06495 discloses a homocysteine synthase (O-succynil-L-homoserine sulfhydrylase) amino acid sequence. Assays for characterizing the homocysteine synthase activity of a particular peptide are well known in the art. For example, the assay described by Yamagata, *Methods in Enzymology,* 143:478, 1987, can be used, with the appropriate substrate, to characterize the activity of a specific peptide. Genes encoding homocysteine synthase peptides are also referred to herein as metZ.

2. O-acetylhomoserine (OAHS) to Homocysteine

Production hosts can be engineered using known polypeptides to produce homocysteine, or to overproduce homocysteine. One method of increasing the production of products in the methionine biosynthetic pathway is through over expression or the expression of a more active form of homocysteine synthase peptides (EC 2.5.1.49).

As used herein, homocysteine synthase includes homocysteine synthase peptides (EC 2.5.1.49), as well as any other peptide capable of catalyzing the conversion of O-succinylhomoserine (OAHS) to homocysteine. The conversion of OAHS to homocysteine through reaction with sulfide is referred to herein as direct sulfhydrylation. Additionally, one of ordinary skill in the art will appreciate that some homocysteine synthase peptides will catalyze other reactions as well, for example some homocysteine synthase peptides will accept other substrates in addition to OSHS, for example the homocysteine synthase described in Example 2, below accepts either OAHS or OSHS as a substrate, such non-specific homocysteine synthase peptides are, therefore, also included. Homocysteine synthase peptide sequences that are publicly available. For example, GenBank Accession Nos: AE004091 REGION: 5655648 . . . 5656925, Y10744 REGION: 1485 . . . 2813, NZ_AAAH02000004 REGION: 164536 . . . 165990 and NZ_AAAY02000081 REGION: complement(12750 . . . 14054) disclose homocysteine synthase (O-acetyl-L-homoserine sulfhydrylase) nucleic acid sequences and GenBank Accession Nos: AAG08410, CAA71732, ZP_00766366, and ZP_00107219 disclose homocysteine synthase (O-acetyl-L-homoserine sulfhydrylase) amino acid sequences. Assays for characterizing the homocysteine synthase activity of a particular peptide are well known in the art. For example, the assay described by Yamagata, *Methods in Enzymology,* 143:478, 1987, can be used, with the appropriate substrate, to characterize the activity of a specific peptide. Genes encoding homocysteine synthase peptides are also referred to herein as metY.

H. Transsulfuration

1. O-succinylhomoserine (OSHS) or Acetylhomoserine (OAHS) to Cystathionine

Production hosts can be engineered using known polypeptides to produce cystathionine, or to overproduce cystathionine. One method of increasing the production of products in the methionine biosynthetic pathway is through over expression or the expression of a more active form of cystathionine γ-synthase peptides (EC 2.5.1.48).

As used herein, cystathionine γ-synthase includes cystathionine γ-synthase peptides (EC 2.5.1.48), as well as any other peptide capable of catalyzing the conversion of OSHS or OAHS to cystathionine. Additionally, one of ordinary skill in the art will appreciate that some cystathionine γ-synthase peptides will catalyze other reactions as well, for example some cystathionine γ-synthase peptides will accept other substrates in addition to OSHS or OAHS. Such non-specific cystathionine γ-synthase peptides are, therefore, also included. Cystathionine γ-synthase peptide sequences are publicly available. For example, GenBank Accession Nos: NC_006958, NZ_AAWW01000006 and NC_004129 disclose cystathionine γ-synthase nucleic acid sequences and GenBank Accession Nos: NP_418374, YP_348978 and NP_601979 disclose cystathionine γ-synthase peptide sequences. Assays for characterizing the cystathionine γ-synthase activity of a particular peptide are well known in the art. For example, the assay described in Methods in Enzymology, 17:425-433, 1971, can be used to characterize the activity of a specific peptide. Genes encoding cystathionine γ-synthase peptides are also referred to herein as metB.

2. Cystathionine to Homocysteine

Production hosts can be engineered using known polypeptides to produce homocysteine, or to overproduce homocysteine. One method of increasing the production of products in the methionine biosynthetic pathway is through over expression or the expression of a more active form of cystathionine β-lyase peptides (EC 4.4.1.8).

As used herein, cystathionine β-lyase includes cystathionine β-lyase peptides (EC 4.4.1.8), as well as any other peptide capable of catalyzing the conversion of cystathionine to homocysteine. Additionally, one of ordinary skill in the art will appreciate that some cystathionine β-lyase peptides will catalyze other reactions as well, for example some cystathionine β-lyase peptides will accept other substrates in addition to cystathionine. Such non-specific cystathionine β-lyase peptides are, therefore, also included. Cystathionine β-lyase peptide sequences are publicly available. For example, GenBank Accession Nos: NZ_AAWW01000001, NC_006958 and NZ_AAVY01000004 disclose cystathionine β-lyase nucleic acid sequences and GenBank Accession Nos: NP_746463, YP_226552 and NP 417481 disclose cystathionine β-lyase peptide sequences. Assays for characterizing the cystathionine β-lyase activity of a particular peptide are well known in the art. For example, the assay described in *Methods in Enzymology,* 143:483-486, 1987, can be used to characterize the activity of a specific peptide. Genes encoding cystathionine β-lyase peptides are also referred to herein as metC.

I. Homocysteine to Methionine

Production hosts can be engineered using known polypeptides to produce methionine, or to overproduce methionine. One method of increasing the production of products, such as methionine or SAMe in the methionine biosynthetic pathway is through over expression or the expression of a more active form of homocysteine methylase peptides (EC 2.1.1.14 and 2.1.1.13).

As used herein, homocysteine methylase includes homocysteine methylase peptides (EC 2.1.1.14, and 2.1.1.13), as well as any other peptide capable of catalyzing the conversion of homocysteine to methionine. Additionally, one of ordinary skill in the art will appreciate that some homocysteine methylase peptides will catalyze other reactions as well, for example some homocysteine methylase peptides will accept other substrates in addition to homocysteine. Such non-specific homocysteine methylase peptides are, therefore, also included. Homocysteine methylase peptide sequences are publicly available. For example, GenBank Accession Nos: NC_004129, NC_006958 and NC_000913 disclose homocysteine methlyase nucleic acid sequences and GenBank Accession Nos: AP_004520, YP_225791 and CAK16133 disclose homocysteine methlyase peptide sequences. Assays for characterizing homocysteine methlyase activity of a particular peptide are well known in the art. For example, the assay described in Analytical Biochemistry, 228, 323-329, 1995, can be used to characterize the activity of a specific peptide. Genes encoding homocysteine methlyase peptides are also referred to herein as metH or metE.

J. Methionine to S-adenosylmethionine

Production hosts can be engineered using known polypeptides to produce S-adenosylmethionine (SAMe), or to overproduce SAMe. One method of increasing the production of products, in the methionine biosynthetic pathway is through over expression or the expression of a more active form of methionine adenosyltransferase peptides (EC 2.5.1.6). One of ordinary skill in the art will appreciate that in instances where methionine is the desired product, the activity or expression of methionine adenosyltransferase peptides (EC 2.5.1.6) encoded by metK, may be attenuated.

As used herein, methionine adenosyltransferase includes methionine adenosyltransferase peptides (EC 2.5.1.6), as well as any other peptide capable of catalyzing the conversion of methionine to SAMe. Additionally, one of ordinary skill in the art will appreciate that some methionine adenosyltransferase peptides will catalyze other reactions as well, for example some methionine adenosyltransferase peptides will accept other substrates in addition to methionine. Such nonspecific methionine adenosyltransferase peptides are, therefore, also included. Methionine adenosyltransferase peptide sequences are publicly available. For example, GenBank Accession Nos: NC_002516, NC_006958 and NC_000913 disclose methionine adenosyltransferase nucleic acid sequences and GenBank Accession Nos: NP_747070, CAI37180 and NP_600817 disclose methionine adenosyltransferase peptide sequences. Assays for characterizing the methionine adenosyltransferase activity of a particular peptide are well known in the art. For example, the assay described in *Methods in Enzymology*, 94: 219-222, 1983, can be used to characterize the activity of a specific peptide. Genes encoding methionine adenosyltransferase peptides are also referred to herein as metK.

II. Genetic Engineering of Production Strain to Increase Methionine Production

Aspartate production can be increased using any method known in the art. For example, aspartate production can be increased by increasing the amount of oxaloacetate produced by the cells with several different approaches. (Gokam et.al, *Appl. Microbiol. Biotechnol.*, 56:188-95, 2001; Sanchez et.al, *Metabolic Eng.*, 8:209-226, 2006).

The production of product can also be increased by over expressing various genes in the L-methionine biosynthetic pathway. For example, genes such as metA, metB, metC, metE, and metH, cysD, cysN, cysC, cysH, cysI, cysJ, cysK and cysM can be placed under the control of a variety of promoters thus allowing higher amounts of these enzymes to be produced.

The metA gene encodes homoserine succinyltransferase which is the first enzyme in the methionine biosynthesis pathway from homoserine and a regulation point for methionine production. The metA protein is a temperature sensitive protein of 186 amino acid residues with a calculated molecular mass of 35.7 kDa. The metA activity is known to be inhibited by the end-products, methionine and S-adenosylmethionine (Lee et al., *J. Biol. Chem.* 241:5479-5780, 1966). Feedback inhibition by these two products is synergistic, meaning that low concentrations of each metabolite alone are only slightly inhibitory, while in combination a strong inhibition is exerted. Thus, a production strain could benefit from a feedback inhibition resistant MetA activity.

Another gene that can be attenuated or deleted in the methionine production strain is mea. The peptide encoded by metJ regulates the expression of several genes involved in methionine biosynthesis pathway. The protein encoded by metJ binds to S-adenosyl methionine and represses the metA, metC, and metF genes.

The protein encoded by the metF gene, 5,10-methylenetetrahydrofolate reductase, is involved in the synthesis of N(5)-methyltetrahydrofolate which is a methyl group donor for L-methionine production from homocysteine (Sheppard et al., *J. Bacteriol.* 181:718-25, 1999). US 2002/0049305 discloses that the production of L-methionine can be improved by increasing the expression of 5, 10-methylenetetrahydrofolate reductase (metF) in *Corynebacteria*. Accordingly, the engineered microorganisms described herein can also be engineered to increase metF production.

The modulation of the gene metK can also increase methionine and SAMe production. S-adenosylmethionine (SAMe) is the primary methyl group donor in all organisms and is involved in polyamine biosynthesis. SAMe is also known as methionine adenosyltransferase (MAT or MetK, EC 2.5.1.6). MetK catalyzes the only known route for SAMe biosynthesis. The complete tripolyphosphate chain is cleaved from ATP and the sulfonium compound is formed.

The formation of SAMe decreases the concentration of methionine and reduces the activity of the methionine biosynthetic pathway via feed back inhibition of MetA. Hence, functionally deleting or attenuating metK can increase methionine production.

One of ordinary skill in the art will appreciate that the efficiency of sulfur utilization by any cell that is making methionine is important. This is especially true for microorganisms that utilize phosphoadenylylsulfate (PAPS) as an intermediate during sulfur assimilation, because making PAPS requires the expenditure of a-molecule of ATP.

Sulfate is fairly unreactive and must first be converted to a more reactive form in order to be used by the cell. In *E. coli* sulfate is incorporated in the cell by a periplasmic transport system, composed of three cytoplasmic membrane components and a substrate specific binding protein located in the periplasmic space. The three membrane components of the sulfate permease are encoded by the cysT, cysW, and cysA genes (cysA locus). The products of the cysA locus are regulated in concert with the rest of the sulfate-assimilation pathway as part of the cys regulon. Sulfate is then activated by coupling to a nucleoside to make high-energy nucleoside phosphosulfates via a pathway that appears to be similar in most organisms.

Figure 6:
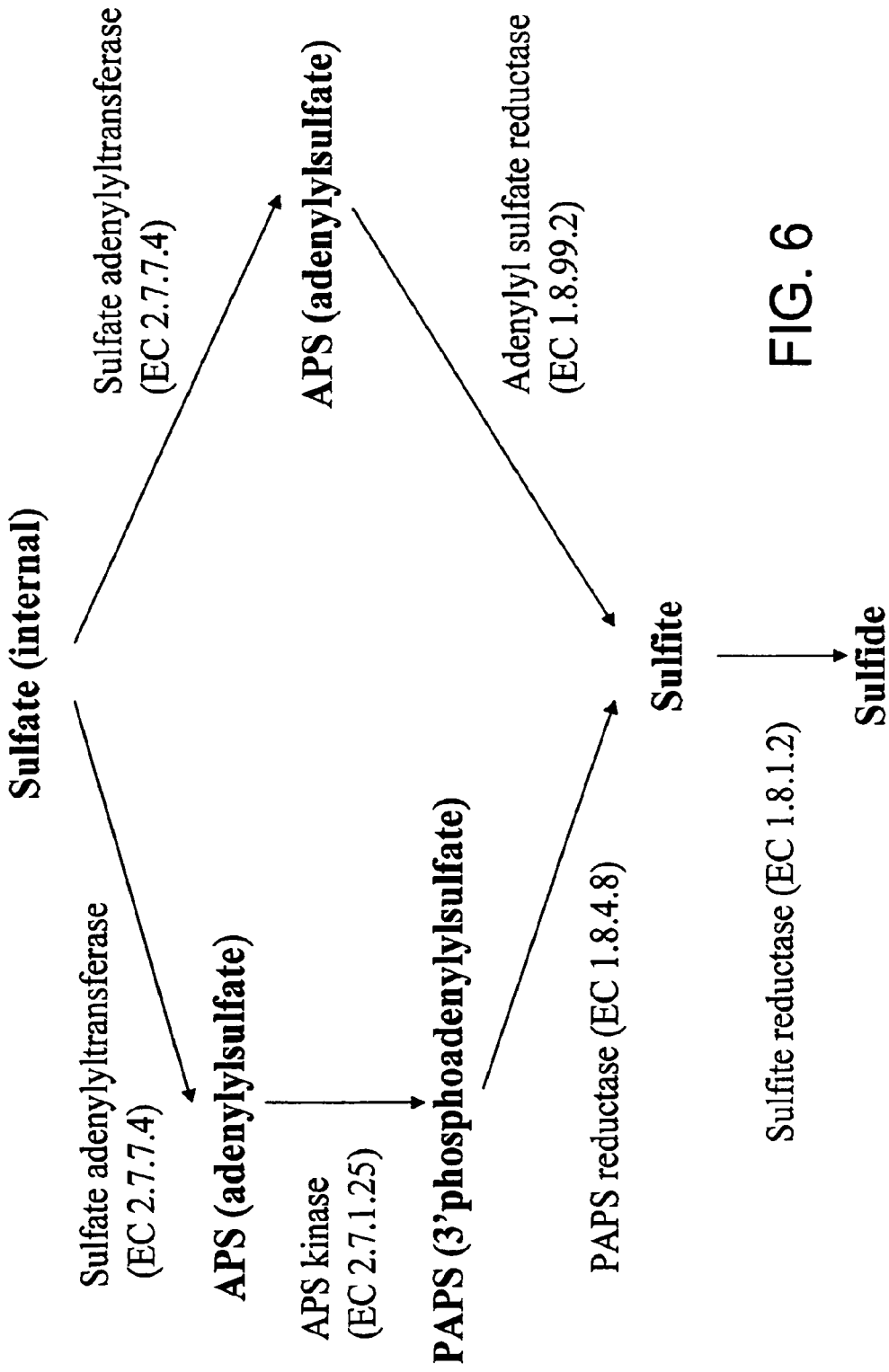
FIG. 6 shows the native sulfur assimilation pathway and a novel alternative one.

As shown in FIG. 6, a microorganism such as *E. coli* utilizes a pathway that converts sulfate to adenylylsulfate (APS) using a sulfate adenylyl transferase peptide (EC 2.7.7.4 coded by cysNcysD). The APS is then converted to PAPS by APS kinase (EC 2.7.1.25 encoded by cysC). This step requires one ATP. PAPS is converted to sulfite by a PAPS reductase (EC 1.8.4.8 coded by cysH) and sulfite is reduced to sulfide by NADPH-sulfite reductase (EC1.8.1.2 coded by cysIcysJcysG). The alternate pathway, shown on the right side of FIG. 6, converts APS directly to sulfite using an adenylyl sulfate reductase (EC 1.8.9.92 or 1.8.4.9). One of ordinary skill in the art will appreciate that any adenylyl sulfate reductase that can convert APS to sulfite will work. For example, the adenylyl sulfate reductase from *Bacillus subtilis* (Accession number CAA04409), or from *Pseudomonas aeruginosa* (Accession number NP_250447).

Adenylyl sulfate reductase encoding nucleic acid sequences can be introduced into any microorganism used to produce methionine. For example the strains described herein, as well as the strains described in WO2005/108561 and WO2006138689 by Metabolic Explorer, and those described by Kumar and Gomes, *Biotechnology Advances*

23:41-61, 2005, can benefit from the disclosed route bypassing PAPS and thus requiring one less ATP molecule for sulfate assimilation.

EXAMPLES

Example 1

Multiple Methionine Production Pathways, One of which Utilizes Direct Sulfhydrylation, using Exogenously Expressed Nucleic Acid Sequences A. Construction of a microorganism having both metABC (Transsulfuration) and metAZ (Direct Sulfhydrylation)

As described before, endogenous production of methionine in *E. coli* occurs mainly through the transulfuration reaction. This Example describes the engineering of *E. coli* to increase direct sulfhydrylation while also maintaining the endogenous metABC pathway.

Direct sulfhydrylation was increased by cloning O-succinylsulfhydrylase (EC 4.2.99.-) which converts O-succinylhomoserine to homocysteine by reacting with hydrogen sulfide. This enzyme is codified by metZ and can be found in some *Pseudomonas* species (Vermeij and Kertesz, *J Bacteriol.* 181: 5833-5837, 1999 and Inoue et al., *J. Bacteria* 179:3956-3962, 1997).

More specifically, metZ from *Pseudomonas aeruginosa* was cloned into methionine auxotrophs of strain TF4076BJF, which was derived from threonine-producing strain TF4076, (additionally modified by the deletion of thrB and metJ, and the insertion of metF under the control of the pTrc promoter, further described in Example 3, below). These auxotrophs have deletion of either the metB or the metB and metC genes. metZ from *Pseudomonas aeruginosa* enhanced the growth of the metB and the metBC deletion mutants in minimal medium. Even though in flask cultures methionine production was not fully recovered, metZ expression induces the methionine production up to ~100 mg/L in metBC deletion mutant, as shown in Table 1. This indicates that metZ is responsible for the production of homocysteine in the cell.

Low methionine production of the deletion mutants transformed with metZ may be due to the limitation of sulfide in the intracellular fraction (methods of increasing sulfide concentration are provided below). This is supported by the finding that the growth of the metBC deletion strain transformed with metZ was enhanced in M9 media in the presence of 2 mM sodium sulfide. In in-vitro assays, the O-succinylsulfhydrylase had low sulfide affinity. Through directed evolution, it is possible to develop improved O-succinylsulfhydrylases with higher sulfide affinity and also higher activity. A highly active O-succinylsulfhydrylase could replace metB and metC in the methionine pathway, or could complement the pathway to increase the carbon flux to methionine.

TABLE 1

Growth complementation and methionine production on TF4076BFJ-ΔBC

| TF4076BJF-ΔBC | OD | glucose used (g/L) | met intermediate (mg/L) OSH | met | GA and HS (g/L) HS | GA |
|---|---|---|---|---|---|---|
| empty vector | 2.5 | 10.0 | 3867 | 0.0 | 0.0 | 0.4 |
| pCL-metB | 20.9 | 38.1 | 0.0 | 0.0 | 0.6 | 0.2 |
| pCL-metB-metC | 9.7 | 40.0 | 0.0 | 670 | 4.36 | 2.4 |
| pPro-metZ | 13.0 | 40.0 | 0.0 | 101 | 3.1 | 4.3 | pCL-metB: metB with its own promoter in pCL1920
pCL-metB-metC: metB and metC with their own promoters in pCL1920
pPro-Z: metZ from *Pseudomonas aeruginosa* in pProLar vector (ClonTech)

B. Construction of a Microorganism Having Both metABC (Transsulfuration) and metXY (Direct Sulfhydrylation)

This example shows simultaneous methionine production from two pathways in *E. coli*. One pathway is the endogenous metABC pathway and the second pathway allows for direct sulfhydrylation via the expression of metY and metX from various organisms.

As shown in FIG. 1 *E. coli* produces methionine endogenously using the transsulfuration pathway genes metA, metB and metC and goes through OSHS. Genetic engineering was used to add an additional pathway to *E. coli* by cloning and expressing the genes metX and metY into *E. coli*, which resulted in a host organism that makes methionine through both transsulfuration and direct sulfhydrylation simultaneously.

The metY and metX genes used to construct the heterologous pathway were cloned from *Leptospira meyeri*, *Deinococcus radiodurans*, *Chloroflexus aurantiacus*, *Brevibacterium linens*, *Nostoc punctiforme* and *Pseudomonas aeruginosa* DNA as described below, and several different strains were constructed to analyze the impact of the addition of these genes on methionine production. The homocysteine synthase from *Corynebacterium glutamicum* and *Saccharomyces cerevisiae* were also cloned and tested. Both pathways were demonstrated to work simultaneously and methionine production was improved with this addition.

To evaluate whether the *L. meyeri* metX and metY enzymes could complement the growth of an *E. coli* methionine auxotroph, the *L. meyeri* metYX gene cluster was amplified from plasmid metXY-pCR2.0-TOPO and cloned into the pPRO-Nde-del vector. The transcription of the metYX genes in this plasmid was initiated by a lac/ara promoter located on the vector.

Four *E. coli* strains including W3110 ΔmetA (stopping production of OSHS), TF4076BJF (increased homoserine production), TF4076BJF ΔmetA (stopping production of OSHS), and TF4076BJF ΔmetAmetB (stopping production of OSHS and cystathionine from OAHS or OSHS) were evaluated. Strain TF4076BJF is a threonine auxotroph, deregulated for methionine production with an increase carbon flux up to homoserine, which is able to produce methionine through the natural *E. coli* pathway.

The strains were transformed with the cloning vector and the plasmid containing metYX, respectively. The transformants were then streaked onto M9 minimal medium plates containing glucose (2 g/L), isoleucine (0.15 g/L), threonine (0.3 g/L), kanamycin (50 mg/L), and IPTG. The metYX gene cluster from *Leptospira meyeri* complemented the growth of W3110 ΔmetA within 24 hrs. The W3110ΔmetA strain expressing only metX was not able to grow on the M9 minimal plate. Therefore, *E. coli* W3110 lacks an efficient enzyme to use O-acetyl-L-homoserine as the precursor for methionine biosynthesis. Strain W3110ΔmetA transformed with the control empty vector, pPRO-Nde-del, as described in WO2006113897, did not grow within 48 hrs. Strain TF4076BJF grew on the minimal medium plates when transformed with either the cloning vector or the plasmid containing metYX from *L. meyeri*.

Alternative metYX genes were also tested for growth complementation in minimal medium. In cloning the metYX genes from *D. radiodurans*, *C. aurantiacus*, *B. linens*, *N. punctiforme*, the translation of the metX gene was coupled with the translation of the metY gene initiated by a rbs located on the vector, due to the absence of an efficient *E. coli* ribosomal binding site (rbs) adjacent to the downstream gene, metX.

The metYX gene cluster from *L. meyeri, D. radiodurans* and *C. aurantiacus* were the most efficient in complementing the growth of the methionine auxotrophic strains. The complementation of growth was also observed in a methionine auxotroph where metY (*L. meyeri*) was replaced with the metY (*P. aeruginosa*) in the *L. meyeri* metYX gene cluster. These cells showed a reduced growth rate relative to the same methionine auxotroph expressing the *L. meyeri* metYX.

Methionine production was determined using the shake flask protocol described in Example 3. Briefly, cultures were grown at 30° C. for 50 hours in the medium supplemented with 150 mg/L of methionine (to improve initial growth) and methionine was measured by HPLC. Table 2 shows that the production of methionine was higher in the strains that carried both pathways compared to those where only the transsulfurylation or the direct sulfhydrylation was available.

TABLE 2

Methionine Production

| Strain | OD | Glucose used g/L | Methionine Produced (final – initial) mg/L |
|---|---|---|---|
| TF4076BJF | 8.2 | 40.0 | 439 |
| TF4076BJF metYX(Lm) | 10.2 | 36.5 | 984 |
| TF4076BJF metY(Pa)metX(Lm) | 9.2 | 29.1 | 299 |
| TF4076BJF metYX(Dr) | 8.8 | 40.0 | 510 |
| TF4076BJF metYX(Ca) | 12.1 | 40.0 | 740 |
| TF4076BJF ΔmetA metYX(Lm) | 5.8 | 23.6 | 368 |
| TF4076BJF ΔmetA metY(Pa)metX(Lm) | 6.6 | 21.1 | 79 |
| TF4076BJF ΔmetAB metYX(Lm) | 6.2 | 23.7 | 280 |
| TF4076BJF ΔmetAB metYX(Dr) | 6.6 | 32.6 | 140 |

Genes metA, and metB are needed for the synthesis of methionine in *E. coli* strains. When either one of the genes is inactivated, *E. coli* loses de novo methionine production capability. The data above indicate that the addition of the metYX operon restores methionine production to levels similar to those obtained with a methionine prototroph. Methionine production was in some cases more than double when both pathways are available to the cell. These results demonstrate that the pathways are not mutually exclusive and that homoserine is converted to methionine via both routes.

Figure 2:
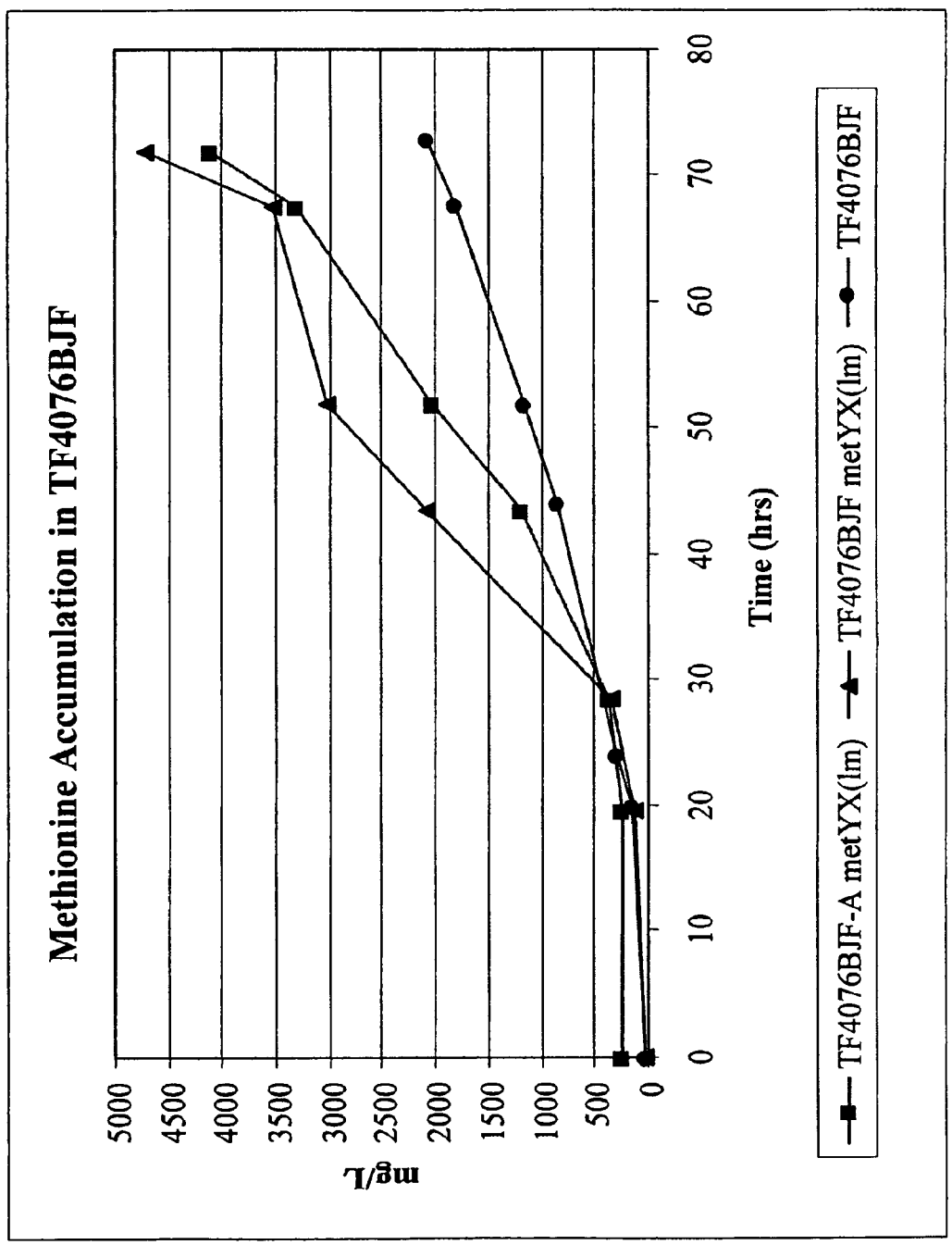
FIG. 2 is a graph showing accumulation of methionine in TF4076BJF, with only transsulfuration activity (TF4076BJF), only sulfhydrylation activity (TF4076BJF-A), or both simultaneously (TF4076BJF metYX(Lm)).

To further demonstrate the benefits of the dual pathway, the strains were compared in 5 Liter fermentation vessels using the fermentation protocol described in Example 3. Methionine accumulation started after approximately 24 hours and continued until the feed was stopped. The enzyme coded by the metY gene from most organisms is feedback inhibited by high concentrations of methionine. In some cases, the enzyme coded by the metX gene is also feedback inhibited. As a result, significant accumulation of homoserine and OAHS were observed in these fermentations. A comparison of methionine production in fermentors is shown in FIG. 2 and the data are summarized in Table 3. These results confirmed the observation seen in the flasks, that the production of methionine could be enhanced significantly by the adequate expression of a heterologous direct sulfhydrylation pathway, and that this pathway could be responsible for the majority of the methionine production if the enzymes were properly expressed.

TABLE 3

Heterologous expression of direct sulfhydrylation pathway

| Strain | Methionine accumulation g/L | O-Acetylhomoserine accumulation (g/L) |
|---|---|---|
| TF4076BJF | 2.1 | — |
| TF4076BJF metYX(Lm) | 4.7 | 7.7 |
| TF4076BJF metY(Pa)metX(Lm) | 1.5 | 20.0 |
| TF4076BJF metYX(Dr) | 4.7 | 32.4 |
| TF4076BJF metYX(Ca) | 4.9 | 20.7 |
| TF4076BJF ΔmetA metYX(Lm) | 4.1 | 6.2 |

To increase the flow of products through to methionine, a metY and a metX that are feedback inhibition resistant can be used. It is also possible to regulate the level of expression of metX and the expression of metH to drive the homoserine faster to methionine.

The differences in methionine production indicate that the metXY pathway is highly effective in *E. coli* and that the metXY pathway added to a deregulated strain such as this can result in more than double the accumulation of methionine.

Example 2

Homocysteine Synthase that Utilizes Either O-acetyl L-homoserine (OAHS) or O-succinyl L-homoserine (OSHS)

This example describes methods used to isolate a homocysteine synthase encoded by metY from *Pseudomonas aeruginosa* (ATCC 47085). This enzyme is inhibited by both L-methionine and S-adenosyl L-methionine. The enzyme activity was analyzed according to Yamagata, *Methods in Enzymology*, 143:478, 1987. The method was slightly modified in that multiple samples points were taken, guanidine was used to quench the reaction and the formation of homocysteine was detected using DTNB ((5,5-Dithiobis(2-nitrobenzoic acid) Sigma D8130) as in the analysis for metA described in Example 3.B. One enzyme unit (U) was defined as the formation of one μmole of homocysteine per minute at room temperature.

MetY from *P. aeruginosa* was expressed and analyzed using 17.5 μg of purified protein (N-tagged). In contrast to the metY from *L. meyeri* and to most other published homocysteine synthases, this enzyme was active with both acetyl and succinyl-homoserine. The activity was similar for both substrates, it was feedback inhibited by methionine and SAMe and the level of feed back inhibition seemed to be slightly lower when OSHS was the substrate. Some inhibition was observed at 1 mM methionine. With OAHS as substrate, at 10, 50 and 100 mM the enzyme retained about 50%, 19% and 9%, respectively, of the activity it had in the absence of methionine. The activity in the presence of 5 and 10 mM SAMe was approximately 72% and 21% of the original activity. When OSHS was the substrate the activity dropped to 53% and 31% in the presence of 50 and 100 mM methionine and 86% and 19% in the presence of 5 and 10 mM SAMe.

Example 3

Methods of Genetically Engineering Host Stains to Increase the Production of Methionine In addition to adding methionine biosynthetic pathways to host organisms as described above in Example 1, the host organism can be further genetically engineered to decrease methionine biosynthetic pathway inhibition, increase reactant availability, and/or decrease product catabolism.

A. Inactivation of Methionine Global Repressor and Threonine Kinase Together with Enhanced Expression of 5,10-methylene-tetrahydrofolate Reductase to Increase Methionine Production.

One method of making a methionine production strain is to modify a strain that has already been engineered to produce an amino acid, such as threonine. For example, the threonine producing strain TF 4076, described in Korean Pat. Publication No. 92-8365 (KFCC 10718) can be used, even though it is a methionine auxotroph). Additional example strains include those deposed in ATCC (13070, 13071, 21148, 21149, 21150, 21151, 21272, 21277, 21278, 21318, 21319, 21320) that are described as threonine overproducers.

Using strain TF 4076 as a starting point, methionine production was enhanced by deleting the thrB gene to avoid threonine production and deleting the metJ gene to release the repression of the expression of the methionine biosynthetic pathway. The strain was also modified to overexpress the metF gene.

thrB Deletion thrB was deleted using a loxP-chloramphenicol (loxP-Cm) cassette (Gene 2000 vol. 247, p255-264). The thrB gene was cloned by PCR using primer sequences 1 and 2 (SEQ ID NOS: 5 and 6) using the chromosome from *E. coli* K12 as a template. PCR conditions of 94° C. for 30 seconds; then 25 cycles of 94° C. for 30 seconds, 55° C. for 30 seconds, and 72° C. for 3 minutes; and 72° C. for 7 minutes, with HL PCR premix (Bioneer Co, Korea) were used. PCR products were gel eluted and cloned into the pCR2.1-topo cloning kit (Invitrogen, USA) and named pCR-thrB. pCR-thrB was digested using pflMI and the loxP-Cm cassette was inserted. From this plasmid, the thrB gene containing loxP-Cm cassette was PCR amplified using primers 1 and 2 (SEQ ID NOS: 11 and 12). The PCR products were gel purified. The PCR fragments were electroporated into the TF4076 strain and chloramphenicol resistant colonies were selected and confirmed for thrB deletion. The chloramphenicol marker was removed from an identified colony and the final strain obtained was named TF4076B. This strain did not grow on M9 minimal medium (DIFCO) without threonine, indicating that this strain is a threonine auxotroph.

```
1. thrB
                                SEQ ID NO: 11
5'- GCT AGC c atg gtt aaa gtt tat gcc ccg -3'

2. thrB
                                SEQ ID NO: 12
5'- GAG CTC tta gtt ttc cag tac tcg tgc gc -3'
``` metJ Deletion

To delete the methionine global repressor metJ gene, the FRT one step deletion method was used (Datsenko and Wanner *PNAS* 97:6640-6645, 2000). PCR fragments were amplified using primer sequences 3, 4 (SEQ ID NOS: 13 and 14) and template pKD3 (see, Datsenko and Wanner, *PNAS* 97:6640-6645, 2000). The PCR conditions used were 94° C. for 30 seconds; followed by 25 cycles of 94° C. for 30 seconds, 55° C. for 30 seconds, and 72° C. for 1 minute; then 72° C. for 7 minutes, with HL PCR premix (Bioneer Co., Korea). Chloramphenicol resistant colonies were selected and the metJ gene deletion was confirmed using PCR primer sequences 5 and 6 (SEQ ID NOS: 15 and 16). Using pCP20 plasmid transformation, the chloramphenicol marker gene was removed and the removal was confirmed using PCR. The strain obtained was named as TF4076BJ.

```
3. metJ + chloramphenicol
                                SEQ ID NO: 13
5'-atggctgaat ggagcggcga atatatcagc ccatacgctg agcacggcaa ggtgtaggct ggagctgctt c-3'

4. metJ + chloramphenicol
                                SEQ ID NO: 14
5'-gtattcccac gtctccgggt taatccccat ctcacgcatg atctccatat gaatatcctc cttag-3'

5. metJ
                                SEQ ID NO: 15
5'-gggctttgtc ggtgaaatg-3'

6. metJ
                                SEQ ID NO: 16
5'-actttgcgat gagcgagag-3'
``` metF Integration

To complement the methionine auxotrophy of TF4076BJ, the metF gene was expressed in strain TF4076BJ. The metF gene was amplified using primer sequences 7 and 8 (SEQ ID NOS: 17 and 18) and the chromosome of *E. coli* K12 strain as the template. PCR conditions of 94° C. 30 seconds, then 25 cycles of 94° C. 30 seconds, 55° C. 30 seconds, 72° C. 1 minute, and then 72° C. 7 minutes and HL PCR premix (Bioneer Co., Korea) were used. PCR fragments were gel eluted and inserted into the NheI and SacI sites in the pSE380 vector (Invitrogen Co.). The plasmid was named pSE380-metF. pSE380-metF was transformed into the TF4076BJ strain. The transformant grew on M9 minimal medium (Difco) containing threonine and isoleucine indicating the complementing of methionine auxotrophy.

The expression level of the metF gene under the control of two different promoters was determined. The promoters were the pCJ1 promoter (PCT/KR2005/004338) and the pThreonine promoter. The metF gene was amplified using primer sequences 9 and 10 (SEQ ID NOS: 19 and 20) and the chromosome of *Escherichia coli* K12 strain as the template. PCR conditions of 94° C. 30 seconds, then 25 cycles of 94° C. 30 sec, 55° C. 30 sec, 72° C. 1 min, and then 72° C. 7min and HL PCR premix (Bioneer Co., Korea) were used. PCR fragments were gel eluted and ligated into the PvuII and HindIII sites in the pCL1920 vector (Lerner and Inouye, *Nucleic acids Research* 18:4631, 1990) containing the pCJ1 promoter or the pThreonine promoter. The pCJ1 promoter was PCR amplified using primer sequences 11 and 12 (SEQ ID NOS: 21 and 22) and the pThreonine promoter was amplified from the *E. coli* K12 chromosome using primer sequences 13 and 14 (SEQ ID NOS: 23 and 24). The PCR fragments were gel eluted and integrated into the KpnI and EcoRV sites in the pCL1920 vector. The PCR conditions used were the same as above. The plasmid containing the metF gene under the control of the pCJ1 promoter was named pCL-pCJ1-metF and the plasmid containing the metF gene under the control of the pThreonine promoter was named pCL-pThr-metF. Each plasmid was transformed to TF4076BJ strain and methionine production was measured.

A shake flask culture protocol was used to test the strains as follows: a seed culture was incubated at 31° C. for 6 hrs in medium consisting of (in 1 L): 10 g Yeast extract, 6 g Na$_2$HPO$_4$.12H$_2$O, 0.5 g NaCl, 3 g KH$_2$PO$_4$, 2 g glucose, 0.49 g MgSO$_4$.7H2O, 0.015 g CaCl$_2$.2H$_2$O. It was then used to inoculate flasks with the following medium: (1 L): 17 g (NH$_4$)$_2$SO$_4$, 1 g MgSO$_4$.7H$_2$O, 2 g Yeast extract, 0.3 g L-threonine, 10 mg MnSO$_4$.7H$_2$O, 10 mg FeSO$_4$.7H$_2$O, 10 mg Zn SO$_4$, 30 g CaCO$_3$, 40 g glucose, and 2 g KH$_2$PO$_4$ pH 7.2. The flasks were incubated for 64 to 72 hours at 31° C. with shaking at 250 rpm. After centrifugation, culture supernatant was isolated and used for methionine analysis.

For the culture of cells containing the pSE380-metF plasmid, 100 µg/L ampicillin and 0.5 mM IPTG was added in the media. The metF gene under the control of the pCJ1 promoter produced the most methionine as shown in Table 4.

TABLE 4

Methionine production in cells containing various metF expression cassettes

| | OD | glucose used (g/L) | Methionine (mg/L) |
|---|---|---|---|
| TF4076BJ | 7.8 | 34 | 0 |
| TF4076BJ/pSE380-metF | 5.4 | 29 | 130 |
| TF4076BJ/pCL-pCJ1-MetF | 7.4 | 35 | 206 |
| TF4076BJ/pCL-pthr-MetF | 22 | 40 | 136 |

To express the metF gene more stably, metF genes under pTrc, pCJ1, and pThreonine promoters were integrated into the lacZ locus of the TF4076BJ chromosome. Each metF gene was PCR amplified from each plasmid and inserted into the NsiI site in the pBrint vector (Borgne et al., Gene 223: 213-219, 1998). The vectors were transformed into the TF4076BJ strain and a transformant that grew on media containing chloramphenicol at 37° C. was selected and confirmed for metF gene integration into the LacZ locus of the chromosome. Selected colonies were transformed by pJW168 and the chloramphenicol marker was deleted. The cells containing pCJ1-metF gene could not be obtained and the transformant containing pThr-metF cassette did not grow well. Only the cells containing pTrc-metF gene in the LacZ locus grew well. The flask culture of this strain showed ~600 mg/L methionine production in the presence of 0.5 mM IPTG in the media. The final strain containing pTrc-metF gene was named as TF4076BJF and was further analyzed.

In summary, the TF4076BJF strain was derived from threonine-producing strain TF 4076, which was modified by the deletion of thrB and metJ, and the insertion of metF under the control of the pTrc promoter. Table 5 shows the production of homoserine and methionine by TF4076BJF.

TABLE 5

Methionine production of the strain TF4076BJF

| Strain | OD | Glucose used (g/L) | Homoserine production (g/L) | Methionine production (g/L) |
|---|---|---|---|---|
| TF4076BJ | 15.3 | 24.7 | 0.62 | 0 |
| TF4076BJF | 10.6 | 34.7 | 4.2 | 0.64 |

7. metF

SEQ ID NO: 17

5'- GCT AGC c atgagctttttcacgccag -3'

8. metF

SEQ ID NO: 18

5'- GAG CTC ttataaaccaggtcgaaccc -3'

9. metF

SEQ ID NO: 19

5'- CAGCTGatgagctttttcacgccag- 3'

10. metF

SEQ ID NO: 20

5'- AAGCTT ttataaaccaggtcgaaccc- 3'

11. CJ1 promoter

SEQ ID NO: 21

5'- cgg ggt acc acc gcg ggc tta ttc cat tac at- 3'

12. CJ1 promoter

SEQ ID NO: 22

5'- acg cga tat ctt aat ctc cta gat tgg gtt tc- 3'

13. threonine promoter

SEQ ID NO: 23

5'- cgg ggt acc tgg tta caa caa cgc ctg g- 3'

14. threonine promoter

SEQ ID NO: 24

5'- cat gat atc tac ctcg tta cc ttt ggt cg- 3'

Strain TF4076BJF was grown in 5 L fermentors according to the protocol described below, and a production of approximately 2.2 g/L of methionine was obtained in 96 hrs.

5 L fermentations were performed using the following protocol. To compare the effect of the different genes cloned in the E. coli strain, a basic fermentation protocol for 5 Liter jars was used. The inoculum was grown in 25 mL of medium consisting of 10.0 g yeast extract, 4.49 g Na$_2$HPO$_4$.7H$_2$0, 0.5 g NaCl, 3.0 g KH$_2$PO$_4$, 0.49 g MgSO$_4$.7H$_2$O, 0.015 g CaCl$_2$.2H$_2$O, and 2 g/L glucose in 1 L volume. 50 mg/L of the appropriate antibiotic was used depending on the resistance of the strain being tested. After incubation with shaking at 31° C. and 250 rpm for 8-24 hours, the culture was transferred to 200 mL of the same medium and incubated under the same conditions for 16 to 20 hours. This culture was used to inoculate fermentors with 2.5 L of medium.

The fermentation medium consisted of: 17.0 g/L (NH$_4$)$_2$SO$_4$, 2.0 g/L yeast extract, 2.0 g/L KH$_2$PO$_4$, 1.0 g/L L-threonine, 0.3 g/L isoleucine, 0.01 g/L MnSO$_4$-H$_2$O, 0.01 g/L FeSO$_4$-7H$_2$O, 0.01 g/L ZnSO$_4$-7H$_2$O, 1.0 g/L MgSO$_4$-7H$_2$O, 2 mg/L piridoxal, 2 mg/L vitamin B12 and 40 g/L glucose. Antibiotics and IPTG were added depending on the strain being grown. The fermentation temperature was maintained at 31° C., the dissolved oxygen above 30% of saturation and the pH was initially controlled with 28% NH$_4$OH. After the glucose was exhausted, the pH would rise. At that point, a continuous fixed feed would be started, or 100-150 mL aliquots of feed would be added at a time, based on increases in pH. The feed consisted of 4.0 g/L yeast extract, 33 g/L (NH$_4$)$_2$SO$_4$, 3.0 g/L KH$_2$PO$_4$, 1.5 g/L L-threonine, 1.0 g/LMgSO$_4$-7H$_2$O, 2 mg/L vitamin B 12 and 400 g/L glucose. Some minor variations to the medium and feed were introduced depending on the strain. The fermentation proceeded for a total of 72 to 96 hours. Methionine concentration was measured throughout, as well as cell growth by optical density and glucose utilization.

B. Generation of Feedback-Resistant Homoserine Succinyltransferases for Methionine Production An E. coli strain was constructed with the metA and the metB genes deleted. This strain showed homoserine accumulation due to the loss of MetA activity. When the wild-type metA cassette was expressed in this strain, OSHS was produced by MetA activity in the absence of methionine. However, when methionine was added in the media, the strain with wt-metA cassette accumulated homoserine again due to the feedback inhibition of MetA activity. Thus, feed back resistant metA genes can be identified by testing for O-succinyl homoserine accumulation in the presence of methionine. The mutant producing more OSHS in the presence of high amount of methionine in the media contains the most feed-back inhibition resistant metA.

Figure 3:
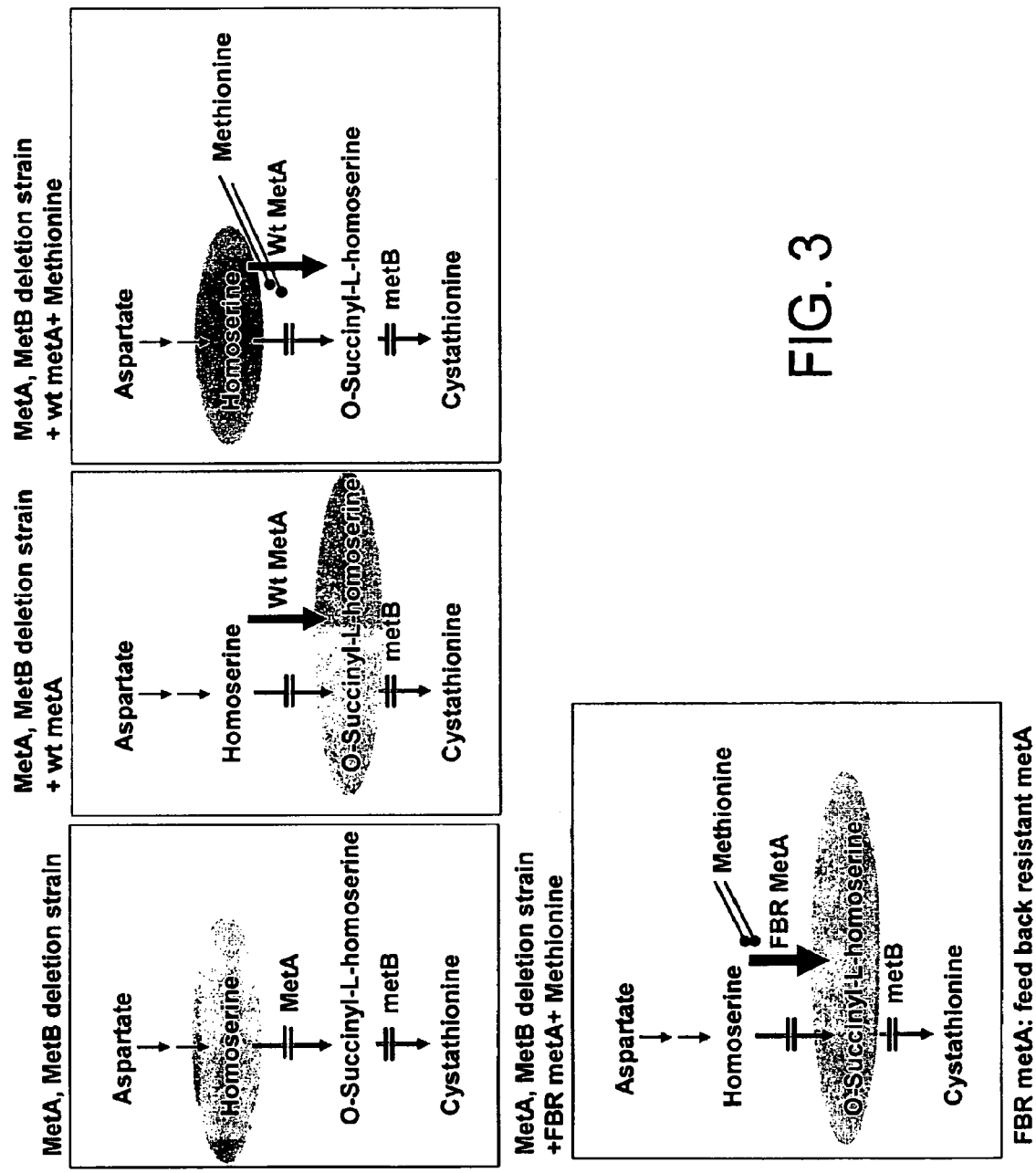
FIG. 3 shows a schematic representation of the screening methodology used to identify metA mutants that are resistant to feed back inhibition. (The product accumulated in each case is shown in the shadowed oval).

A schematic representation of the screening methodology is provided in FIG. 3.

Construction of metB Deletion Mutant

To make a metB deletion mutant in TF4076BJF, the FRT one step deletion method was used (Datsanko and Wanner, *PNAS* 97:6640-6645, 2000). PCR fragments were amplified using primer sequences 15 and 16 (SEQ ID NOS: 25 and 26) and template pKD3 was electroporated into TF4073BJF cells. The PCR conditions of 94° C. 30 seconds, 25 cycles of 94° C. 30 seconds, 55° C. 30 seconds, 72° C. 1 minutes, then 72° C. 7min and HL PCR premix (Korea, Bioneer Co) were used. Chloramphenicol resistant colonies were selected and confirmed for metB gene deletion using PCR. The chloramphenicol marker gene was removed using pCP20 plasmid transformation, and the removal was confirmed by PCR. The strain obtained by this procedure was named as TF4076BJF-B.

```
15. metB + chloramphenicol
                                         SEQ ID NO: 25
5'-TTACTCTGGT GCCTGACATT TCACCGACA AAGCCCAGGG AACTTCATCA Cgtgtaggct ggagctgctt c -3'

16. metB + chloramphenicol
                                         SEQ ID NO: 26
5'-TTACCCCTTG TTTGCAGCCC GGAAGCCATT TTCCAGGTCG GCAATTAAA Tcatatgaat atcctcctta g -3'
```

Construction of metA Deletion Mutant

To make a metA deletion mutant in TF4076BJF-B, the FRT one step deletion method was used (*PNAS* .97:6640-6645, 2000). PCR fragments were amplified using primer sequences 17, 18 (SEQ ID NOS: 27 and 28) and template pKD3 was electroporated into TF4073BJF-B cells. The PCR conditions of 94° C. 30 seconds, 25 cycles of 94° C. 30 seconds, 55° C. 30 seconds, 72° C. 1 minute, then 72° C. 7 minutes and HL PCR premix (Korea, Bioneer Co) were used. Chloramphenicol-resistant colonies were selected and confirmed for metA gene deletion using PCR. The chloramphenicol marker gene was removed using pCP20 plasmid transformation, and the removal was confirmed by PCR. The strain obtained by this procedure was named as TF4076BJF-BA.

```
17. metA + chloramphenicol
                                         SEQ ID NO: 27
5'-
CAATTTCTTGCGTGAAGAAAACGTCTTTGTGATGACAACTT CTCGTGCGTgtgtaggctggagctgcttcc -3'

18. metA + chloramphenicol
                                         SEQ ID NO: 28
5'-
AATCCAGCGTTGGATTCATGTGCCGTAGATCGTATGGCGTG ATCTGGTAGcatatgaatatcctccttag-3'
```

Construction of metA Expression Vector

To make a metA library, a metA expression vector was constructed. The metA gene was amplified using primer sequences 19 and 20 (SEQ ID NOS: 29 and 30) with the chromosome from the *E. coli* K12 strain as the template. The PCR conditions of 94° C. 30 seconds, 25 cycles of 94° C. 30 seconds, 55° C. 30 seconds, 72° C. 1 minute, then 72° C. 7 minutes and HL PCR premix (Korea, Bioneer Co) were used. The PCR fragments were gel eluted and ligated into pCL1920 at the SmaI site. The plasmid was named pA-CL. The pA-CL plasmid was transformed into the TF4076BJF-AB strain and flask culture was performed with and without methionine. OSHS and homoserine were measured by the same method as described above for methionine. As shown in Table 6, the cells containing the pA-CL plasmid in the absence of methionine produced 3.8 g/L OSHS with 0.24 g/L homoserine. However, in the presence of 1 g/L methionine the cells produced 5.8 g/L OSHS with 4.9 g/L homoserine. The increase of OSHS amount is due to the increase of growth by methionine addition, while the increase of homoserine is due to the feed-back inhibition of metA activity by methionine.

TABLE 6

O-succinyl homoserine and homoserine production in TF4076BJF-AB strain containing pA-CL plasmid

| Methionine addition | Strain | OD | Glucose used (g/L) | OSH production (g/L) | HS production (g/L) |
|---|---|---|---|---|---|
| 0 g/L | TF4076BJF-AB /pC11920 | 2.2 | 14.2 | 0 | 1.42 |
| 0 g/L | TF4076BJF-AB /pA-CL | 2.1 | 13.1 | 3.8 | 0.24 |
| 1 g/L | TF4076BJF-AB /pC11920 | 4.7 | 39.8 | 0 | 5.7 |
| 1 g/L | TF4076BJF-AB /pA-CL | 6.4 | 37.4 | 5.9 | 4.9 |

```
19: metA
                                         SEQ ID NO: 29
5'-aatggatccTGCCGTGAGCGGCGAATAC-3'

20: metA
                                         SEQ ID NO: 30
5'-agctctagaCTGCTGAGGTACGTTTCGG-3'
```

Construction of pA-CL Mutant Library

To make a pA-CL mutant library, error-prone PCR was performed. Error-prone PCR was done using the primer sequences 21 and 22 (SEQ ID NOS: 31 and 32) with the pA-CL plasmid as a template. The PCR conditions of 94° C. 30 seconds, 25 cycles of 94° C. 30 seconds, 55° C. 30 seconds, 68° C. 2 minutes, then 72° C. for 7 minutes and BD diversify PCR mutagenesis kit (BD, USA) were used. PCR fragments were digested by BamHI and XbaI and ligated into pCL1920. The library was transformed into strain TF4076BJF-AB and ~30,000 transformants were collected for further analysis.

```
21: pCL1920
                                         SEQ ID NO: 31
5'-CGAAGTAATCGCAACATCCG-3'

22: pCL1920
                                         SEQ ID NO: 32
5'-GTCTGCTATGTGGTGCTATC-3'
```

Preparation of MetB Enzyme Crude Extract

To measure the OSHS by enzymatic method, the MetB enzyme from *E. coli* was used. The MetB enzyme reacts with OSHS and cysteine in a 1:1 ratio and produces cystathionine. The reagent DTNB (5,5-Dithiobis(2-nitrobenzoic acid) Sigma D8130) reacts with the free SH group of cysteine and makes a yellow color which can be measured at 415 nm.

Before the MetB reaction, cysteine reacts with DTNB and turns to yellow color. After the MetB reaction, cysteine turns to cystathionine which can not bind to DTNB. By the decrease of OD at 415 nm after the reaction, the amount of OSHS in the reaction mix can be measured.

For the overexpression of MetB enzyme, the PCR amplified metB gene from E. coli K12 chromosome was digested by BamHI and HindIII and cloned into the pCDF-Duet vector (Novagene, USA). A PCR reaction was performed using the primer sequences 23 and 24 (SEQ ID NOS: 33 and 34) and the E. coli K12 chromosome as the template. The PCR conditions of 94° C. 30 seconds, 25 cycles of 94° C. 30 seconds, 55° C. 30 seconds, 72° C. 1 minute, then 72° C. 7 minutes and HL premix (Bioneer, Korea) were used. The plasmid containing the metB gene was transformed into E. coli using a Tuner cell (Novagen, USA) and the transformant was grown overnight with LB media containing 50 µg/mL spectinomycin. The overnight culture broth was diluted in LB media containing 50 µg/mL spectinomycin and incubated at 37° C. until it reached an OD at 600 nm of 0.6, at which point IPTG was added to a final concentration of 0.2 mM and the culture was incubated for 4 hrs at 30° C. The cells were harvested by centrifugation at 12,000 rpm, resuspended in 0.1 M potassium phosphate buffer (pH 7.5) and ruptured by sonication (5×30 seconds). Crude cell extract was acquired by centrifugation for 20 min at 12,000 rpm and the supernatant was then used for enzyme assay.

```
23: metB
                                       SEQ ID NO: 33
5'-gccaggatccgATGACGCGTAAACAGGCCAC-3'

24: metB
                                       SEQ ID NO: 34
5'-ccgcaagatTTTACCCCTTGTTTGCAGCC-3'
```

Screening of Feed Back Resistant metA

Feedback resistant metA mutations were identified by inoculating the TF4076BJF-AB strain containing pA-CL mutants into 96 well plates containing microfermentation media and culturing for 48 hrs at 31° C. with shaking. Microfermentation media is 1 volume of shake flask media as described in Example 3, and 1 volume of 0.05M potassium phosphate buffer pH 6.5, with 5 g/L L-methionine.

The 96 well plates were then centrifuged for 10 min at 3,000 rpm and OSHS was measured in the supernatant by the enzymatic method described above (Preparation of MetB crude extract). 50 µL of the culture supernatant was mixed with 50 µL of reaction buffer (Reaction buffer: 0.1 M potassium phosphate buffer (pH 7.5)+2.5 mM cysteine+1/500 10 mM PLP (pyridoxal 5'-phosphate hydrate, Sigma P9255)+1/100 MetB crude extract (5 mg/mL)). The reaction was incubated for 10 minutes at 37° C. 100 µL DTNB (4 mg/10 mL 0.1 M potassium phosphate buffer, pH 7.5) was added and the OD at 415 nm was taken. 1 or 2 colonies showing the lowest absorbance at 415 nm were selected from each 96 well plate and they were streaked onto LB media containing 50 µg/mL spectinomycin. The resulting colonies were inoculated onto another 96 well plate containing microfermentation media and a second round of screening was performed. The selected strains were then tested under the shake flask culture conditions described above, with the addition of 5 g/L methionine to the medium, and O-succinylhomoserine production was measured.

24 mutants from 12,000 colonies were selected for flask culture and 14 mutants were selected for sequencing. From those, 5 new mutants were identified. The other remaining 9 mutants possessed the same mutations as had been previously reported. The accumulation of O-SHS and homoserine in shake flask culture for the 14 mutants is shown in Table 7, and the amino acid changes in the metA sequences of the selected mutants are shown in Table 8.

TABLE 7

Shake flask performance of selected mutants

| Strain No | OD | Glucose used (g/L) | OSH production (g/L) | HS production (g/L) |
|---|---|---|---|---|
| Control (TF4076BJF-AB/pA-Cl) | 6.0 | 40 | 4.9 | 5.5 |
| #7 | 4.9 | 40 | 9.2 | 2.9 |
| #8 | 4.6 | 40 | 5.4 | 3.8 |
| #10 | 4.7 | 40 | 8.8 | 3.0 |
| #11 | 4.7 | 40 | 9.1 | 2.8 |
| #32 | 5.8 | 40 | 10.7 | 1.6 |
| #34 | 5.6 | 40 | 10.1 | 2.4 |
| #36 | 5.6 | 40 | 10.4 | 2.2 |
| #37 | 5.9 | 40 | 9.6 | 1.6 |
| #39 | 7.0 | 40 | 9.2 | 1.0 |
| #22 | 4.8 | 40 | 9.4 | 1.4 |
| #23 | 4.6 | 40 | 9.6 | 1.4 |
| #41 | 5.6 | 40 | 11.8 | 2.1 |
| #43 | 6.1 | 40 | 11.2 | 2.3 |
| #47 | 6.0 | 40 | 11.2 | 2.2 |
| #49 | 5.6 | 40 | 11.5 | 2.1 |

TABLE 8

Sequence analysis of selected mutants

| position | wt | 32 SEQ ID NO: 2 | 37 SEQ ID NO: 4 | 10 SEQ ID NO: 6 | 11 SEQ ID NO: 8 | 41 SEQ ID NO: 10 |
|---|---|---|---|---|---|---|
| 24 | T | | S (A70T) | | | |
| 29 | S | | | | P (T85C) | |
| 79 | N | | | | | S (A236G) |
| 114 | E | | | | G (A341G) | |
| 140 | F | | | | S (T419C) | I (T418A) |
| 163 | K | Q (A487C) | | | | |
| 222 | F | L (T666A) | | | | |
| 275 | A | | | E (C824A) | | |
| 290 | N | | | H (A868C) | | |
| 291 | Y | | | | | N (T871A) |
| 295 | Q | R (A884G) | | | | |
| 297 | T | | A (A889G) | | | |
| 304 | M | | | | | L (A910T) |
| 305 | N | | Y (A913T) | | | |

TABLE 8-continued

Sequence analysis of selected mutants

| position | wt | 32 SEQ ID NO: 2 | 37 SEQ ID NO: 4 | 10 SEQ ID NO: 6 | 11 SEQ ID NO: 8 | 41 SEQ ID NO: 10 |
|---|---|---|---|---|---|---|
| no amino acid change | | A105G, A597T | C222T | T450C | T915C | T573C |

Feed Back Resistance of Mutant metA

Since all the feed-back inhibition resistant metAs produced similar amounts of OSHS in the presence of 5 g/L methionine in the flask culture, higher concentrations of methionine were added in the flask culture media and the production of OSHS was determined. After 64 hrs of culture with 30 g/L L-methionine, production of OSHS decreased only in the #37 mutant sample, and all the others showed similar levels of OSHS production as in the presence of 5 g/L methionine. These results, presented in Table 9, indicated that the feedback inhibition resistance metAs were resistant to concentrations as high as 30 g/L methionine.

TABLE 9

OSHS production of mutant metAs in the presence of 30 g/L methionine

| Strain | OD | Glucose used (g/L) | OSH production (g/L) | HS production (g/L) |
|---|---|---|---|---|
| Control (TF4076BJF-AB/pA-Cl) | 4.36 | 38.6 | 2.7 | 1.1 |
| #10 | 3.3 | 33.1 | 10.6 | 0.44 |
| #11 | 3.5 | 36.6 | 11.5 | 0.22 |
| #32 | 3.1 | 30.2 | 10.7 | 0.23 |
| #37 | 2.0 | 22.0 | 6.2 | 0.05 |
| #41 | 4.4 | 40.0 | 10.5 | Not analyzed |

In-vitro Characterization of Mutant metA Proteins

PCR was used to amplify and then clone the five metA mutant genes identified as pCL-A#10, pCL-A#11, pCL-A#32, pCL-A#37, and pCL-A#41, into the pET30a vector. All constructs were subjected to DNA sequence analysis to confirm the presence of mutations. The genes were cloned with a C-terminus His tag for enzyme purification. The enzymes were overexpressed, purified and the activity was measured in the presence of different levels of methionine and SAMe, as described by Lawrence, *J. Bacteriol.*, 109:8-11, 1972. The only modifications to the assay were that multiple points were taken and that the reaction was quenched with guanidine. Table 10 provides a summary of the activity from the various mutants, and clearly shows that all the mutants were feed-back inhibition resistant when compared to the wild type enzyme and that mutants #10 and #11 were the most resistant to both methionine and SAM inhibition.

TABLE 10

Characterization of mutant and wild type MetA enzymes

| Specific activity (U/mg)* | w.t. | #10 SEQ ID NO: 6 | #11 SEQ ID NO: 8 | #32 SEQ ID NO: 2 | #37 SEQ ID NO: 4 | #41 SEQ ID NO: 10 |
|---|---|---|---|---|---|---|
| control | 386 | 176 | 479 | 276 | 228 | 315 |
| w/ 100 mM Met | 29 | 172 | 451 | 218 | 190 | 232 |
| w/ 300 mM Met | — | 125 | 282 | — | — | — |
| w/10 mM SAM | 11 | 150 | 395 | 78 | 63 | 108 |

| % of specific activity retention | w.t. | #10 | #11 | #32 | #37 | #41 |
|---|---|---|---|---|---|---|
| control | 100 | 100 | 100 | 100 | 100 | 100 |
| w/ 100 mM Met | 7.6 | 97 | 94 | 79 | 83 | 74 |
| w/ 300 mM Met | — | 70 | 56 | — | — | — |
| w/10 mM SAM | 2.9 | 85 | 82 | 28 | 27 | 34 |

*Where U is the formation of 1 μmole of CoA per minute at room temperature

Mutants metA#10 and metA#11 (SEQ ID NOS: 5 and 7, respectively) were selected for further analysis. metA mutants #10 and #11 were analyzed for their lack of inhibition in an experiment using 300 mM of methionine. This is close to the highest concentration achievable in the assay conditions. The solubility of methionine in water is 5.6 g/100 mL at 30° C., which corresponds to a concentration of 375 mM. In the presence of 300 mM of methionine, mutant metA#10 retained 70% of its specific activity, and mutant metA #11 retained 55% of its specific activity. Thus, the metA#10 and #11 mutants can be used to in a methionine producing microorganism.

Figure 4:
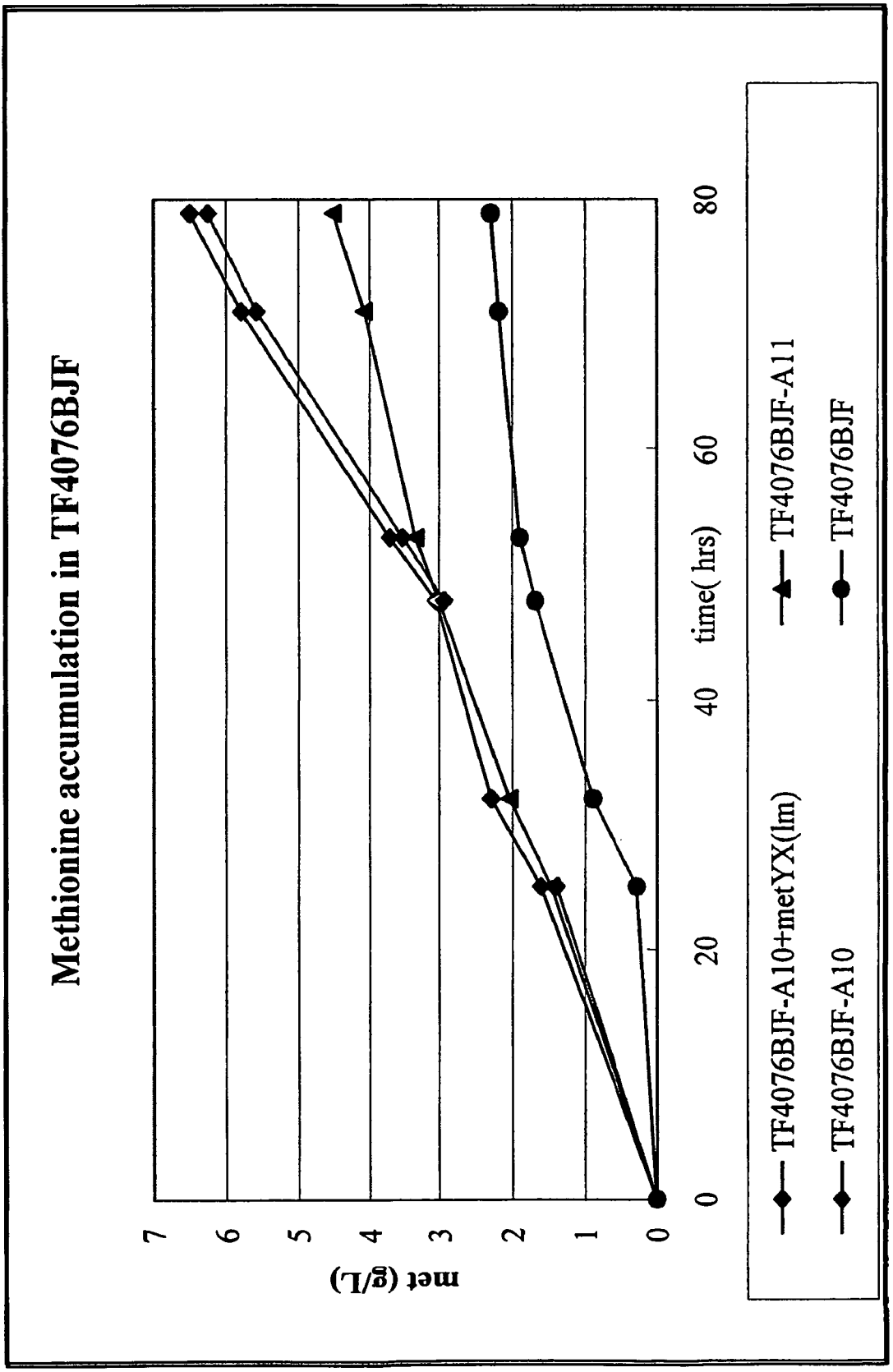
FIG. 4 shows a time course of methionine accumulation produced by a strain expressing feedback inhibition resistant metA genes.

Methionine Production with Feedback Inhibition Resistant metA metA#10 and metA#11 were individually cloned into the methionine producing strain TF4076BJF. MetA#10 was also cloned together with metYX from *L. meyeri*. The clones were tested following the fermentation protocol described in Example 3A. Methionine concentrations were assessed after 78 hours of fermentation and the results are shown in Table 11. There was no O-succinylhomoserine accumulation in any of the fermentations. The time courses of methionine production are shown in FIG. 4.

TABLE 11

Methionine Accumulation

| Strain | Final methionine titer (g/L) |
|---|---|
| TF4076BJF | 2.1 |
| TF4076BJF metA#10 | 6.3 |
| TF4076BJF metA#11 | 4.5 |
| TF4076BJF metA#10 + metYX (Lm) | 6.6 |

These results show that expression of feedback inhibition resistant metAs increased methionine production and that the combination of a direct sulfhydrylation pathway and a feedback inhibition resistant metABC pathway showed less synergy than observed with the native MetA. The less synergy observed indicates that the accumulation of methionine may be inhibiting MetY. To increase methionine production further, a feedback inhibition resistant MetY can be used.

C. Strategies for Attenuation of MetK Activity in *E. coli*

As described above, the formation of SAMe decreases the concentration of methionine and reduces the activity of the methionine biosynthetic pathway via feed back inhibition of metA.

Isolation of mutants in the metK gene are facilitated by the observation that some ethionine-resistant mutants have reduced levels of metK and overproduce methionine. Table 12, lists various metK mutations that have been described as causing a decrease in MetK activity. These mutants were constructed as described below.

The metK gene from *E. coli* (Accession number AP_003499 or BAE77005) was cloned and overexpressed with either an N-terminal or a C-terminal His tag in pET28b vector. Site directed mutagenesis was performed using the C-terminal His tagged metK clone to generate the desired mutants. Expression of the mutant MetK proteins was confirmed.

The MetK mutants were purified (using the C-terminal His tag) and assayed in vitro. The wild type C-terminal His-tagged MetK protein was used as a control. The mutants were assayed using a radioactive assay. The assay conditions were as follows:

Assay Mix:
1.0 mL 0.5 M HEPES/KOH, pH 8.0
0.5 mL 1.0 M KCl
0.2 mL 1.0 M MgCl$_2$
1.0 mL 100 mM ATP (disodium salt, pH 8.0 with KOH)
0.1 mL 50 mM methionine
0.1 mL NEN [methyl-$^{14}$C]methionine
6.6 mL H$_2$O
25 mM EDTA pH 8.0 stop for assays.

45 µl of assay mix was added to an Eppendorf tube and 5 µL of enzyme (normalized data shown in Table 13. The reaction was incubated at room temperature (or 25° C.) for a desired period (1 to 10 minutes). The reaction was stopped with the addition of 150 µL of 25 mM EDTA. 100 µL of the reaction was spotted onto a 2.5 cm diameter Whatman P-81 phosphocellulose filter circle (labeled in pencil). The filters were washed with 3 L of distilled water, air-dried and placed in scintillation vials with aquasol. The emissions were counted using a window that extends from $^{14}$C to about 0. Assay efficiency and quench levels were determined by adding a known amount of counts of pure $^{14}$C-SAM and processing through the whole procedure. Backgrounds are typically <100 cpm (total counts ca. $10^5$ cpm per reaction).

TABLE 12

| Residue | Position | Replacement | Expected Effect on SAMe synth | Reference | Normalized Activity (CPM SAMe/ µg purified protein/min) ** |
|---|---|---|---|---|---|
| His | 14 | Asn | Activity reduced ~ 104 fold | J. Biol Chem 2000 | 7.7 |
| Asp | 16 | Asn | kcat reduction of ~ 103 fold | J. Biol Chem 1999 | 2.5 |
| Gly | 77 | Val | Expected decrease in MetK activity | Markham personal communication | 6.9 |
| Cys | 90 | Ala | Only 10% of WT activity | J. Biol Chem 1995 | Same as WT |
| Cys | 90 | Ser | Only 10% of WT activity | J. Biol Chem 1995 | 23.2 |
| Asp | 118 | Asn | kcat reduction of ~ 103 fold | J. Biol Chem 1999 | 1.3 |
| Val | 185 | Glu | 6.4X increase in excreted Met over control | AEM 2005 | 4.9 |
| Asp | 238 | Asn | kcat reduction of ~ 103 fold | J. Biol Chem 1999 | 1.9 |
| Cys | 239/240 | Ala* | Only 10% of WT activity | J. Biol Chem 1995 | Same as WT |
| Lys | 245 | Met | 42,000 fold lower activity than WT | J. Biol Chem 2000 | 2.5 |
| Asp | 271 | Ala | kcat reduction of ~ 103 fold | J. Biol Chem 1999 | 0.4 (not duplicated) |
| WT control * | | None | | Cargill BioTDC | 995.4 |
| WT | Untagged | None | | Markham lab | 5600 |

* WT control MetK protein was also C-terminal His tagged for comparison with the tagged mutant metK proteins. An approximately 6-fold decrease in activity was observed with the tagged WT MetK protein when compared to untagged MetK protein activity.
**activity for 5 minute reaction time reported The product of the MetK reaction, SAMe, is a non-competitive inhibitor of MetK. Therefore, reaction kinetics are complicated to analyze and it is expected that the difference between the activities of the wild type and the mutants is even higher. By understanding the activity of the various mutant MetK enzymes a suitable production host can be designed.

D. SAMe Transporter Regulation

S-AdenosylMet (SAMe) serves as the primary methyl group donor in all organisms, is involved in polyamine biosynthesis and is essential for cell growth. S-adenosyltransferase (MetK, EC 2.5.1.6) catalyzes the only known route for SAMe biosynthesis in *E. coli*, as this organism cannot uptake SAMe from the growth medium. An alternative to the down regulation of metK as described above is to provide *E. coli* with the ability to uptake SAMe and simultaneously knockout the metK gene, to reduce or avoid utilization of methionine via that route. Cell growth can then be controlled by the addition of SAMe to the fermentation medium.

A Rickettsia high-affinity SAMe transport system has been identified (Tucker et al., *J. Bact.* 185: 3031-3035, 2003). This SAMe transporter has $K_T$ values of 2-8 µM which is comparable to the values for the transporter from *S. cerevisiae* (3.3 µM), *P. carnii* (4.5 µM), and rat liver (8.9 µM). In addition it has been reported that the Rickettsia SAMe transport system can complement an *E. coli* metK deletion mutant (Driskell et al., *J. Bact.* 187:5719-5722, 2005).

The strains W3110 and TF4076BJF were transformed with a plasmid containing the SAM transporter mentioned above. The metK gene from W3110 was knocked-out and verified by PCR. According to these modifications, the new strain should have been able to grow only in the presence of SAM, but not without it. However, it continued to grow in both absence and presence of exogenous SAM.

E. Knock Out of Methionine Uptake Transporters to Increase Methionine in Fermentation Medium Two L-methionine transporters have been, identified in *E. coli*, one with a very high affinity (Km=0.1-0.13 µM) and a second with lower affinity (Km=20-40 µM). The locus for the high affinity transporter system is designated metD since the metD mutants are unable to transport D-methionine and to utilize it as a methionine source. The metD locus corresponds to the abc (metN), yaeE(metI) and yaeC (metQ) genes which encode an ABC transporter necessary for L-methionine and D-methionine uptake. metN encodes the putative ATPase and metI encodes the membrane-spanning region of the metD ABC transporter. It is expected that the third component, metQ, encodes the substrate-binding domain. Since, metI, metN and metQ deletion mutants can still grow in the presence of L-methionine, it is taken to be indirect evidence for the presence of the low affinity metP system.

Figure 5:
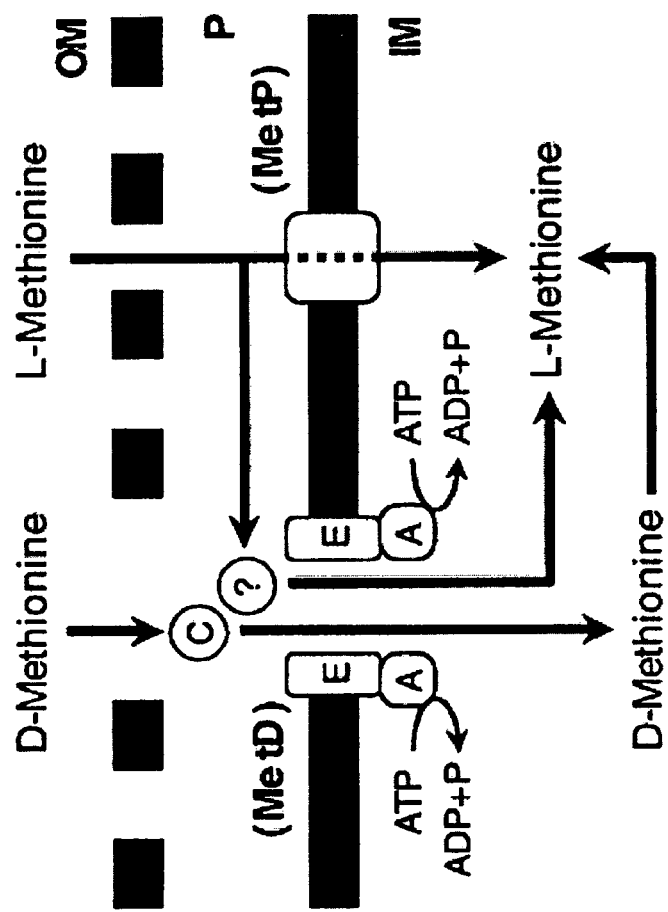
FIG. 5 shows a model of methionine transport in *E. coli*.

As illustrated in FIG. 5, metD imports D- and L-methionine, while the genetically uncharacterized transporter metP imports only L-methionine. MetD is represented as a typical ABC transporter with its three components: A, E, and C represent abc (ATPase), yaeE (permease), and yaeC (D-methionine-binding protein), respectively. (Merlin et al., *J. Bacteriol.* 184: 5513-5517, 2002).

metJ, the global methionine repressor protein, was shown to negatively control expression of the operon encoding the metD locus. Transcription of the metD genes increases upon deprivation of methionine, which is a metJ corepressor. In cells with a metJ deletion, the transporters are more highly expressed and not repressed by methionine (Merlin et al., *J. Bacteriol.* 184: 5513-5517, 2002). Methionine productions strains generally have attenuated metJ sequences or med deletions so, to increase production, it can be particularly important to reduce the methionine import activity. The strains can be modified by knocking out the metD methionine uptake system. This will prevent methionine uptake and avoid the potential energy-wasting futile cycle of uptake/excretion.

Knocking out metD resulted in a 25% increase in methionine accumulation in the fermentation broth, as measured by the shake flask protocol described in Example 3, above.

F. Over Expression of metH

The increase in carbon flux through the methionine pathway due to the modifications to the strains described here, can lead to an accumulation of homocysteine inside the cell. Homocysteine is very toxic to the cell. To avoid any accumulation and convert the homocysteine to methionine, it is very important to have very active homocysteine methylase activity (EC 2.1.1.13 and 2.1.1.14) which are codified by the metE and metH, respectively. One way to accomplish this is to overexpress these genes either in a plasmid system or by placing the chromosomal copy under the control of a strong promoter.

The native metH gene from *E. coli* was overexpressed under several different promoters in a strain containing the dual pathways metABC and metXY, and the methionine production was measured in our standard shake flask protocol. The three vectors used for metH overexpression were pCL-P (cysK), pCL-P(pro), and pCL-P(CJ-1) which were respectively modified from commercially available plasmid pCL1920 by replacing the Plac promoter with the promoter of *E. coli* cysK gene, the promoter from commercial vector pPROLar, and CJ Corporation's proprietary promoter CJ1. The ORF of the *E. coli* metH gene was located just downstream of the promoters. The results obtained are shown in Table 13, below. It was clear that even at the relatively low levels of methionine accumulated in the shake flask protocol, the presence of a high concentration of the homocysteine methylase had a very significant positive effect on the production of methionine. The effect was even more pronounced in fermentors.

TABLE 13

Effect of over-expression of metH on methionine production

| Strains | OD | Glucose used g/L | Methionine Produced mg/L |
| --- | --- | --- | --- |
| TF4076BJF met YX Lm | 7.4 | 40.0 | 868 |
| TF4076BJF met YX Lm pcL-P (cysK) met H | 11.7 | 33.9 | 1289 |
| TF4076BJF met YX Lm pcL-P (pro) met H | 7.5 | 32.8 | 1062 |
| TF4076BJF met YX Lm pcL-P (CJ-1) met H | 12.4 | 40.0 | 1337 |
| TF4076BJF met YX Dr | 10 | 38.2 | 569 |
| TF4076BJF met YX Dr pcL-P (cysK) met H | 15.4 | 40.0 | 896 |
| TF4076BJF met YX Dr pcL-P (pro) met H | 12.5 | 40.0 | 786 |
| TF4076BJF met YX Dr pcL-P (CJ-1) met H | 15 | 40.0 | 856 |

G. Improving Sulfate Uptake and Increasing APS Pool in Methionine Producing Organisms This Example describes a method of engineering *E. coli* to bypass the intermediate, PAPS, in its endogenous sulfur assimilation pathway. The new pathway created requires one less molecule of ATP for each sulfate molecule reduced to sulfide, thus, it is more energy efficient (see, FIG. 6).

As previously described, FIG. 6 shows two ways to take advantage of alternative sulfur assimilation pathways. One way is to clone the adenylyl sulfate reductase, cysH (EC 1.8.4.9) gene from *Bacillus* or *P. aeruginosa* and either incorporate it into the *E. coli* genome or express it from a plasmid. This allows APS to be converted to sulfite in a single step, thus avoiding the conversion of APS to PAPS catalyzed by *E. coli* APS kinase (cysC). The second way would be to mutate the *E. coli* PAPS reductase gene, based on the bacterial cysH homologs, so that its substrate specificity is changed from PAPS to APS.

The cysH genes from *Bacillus subtilis* 168 (Accession number AJ000974 REGION: 548 . . . 1249) and *Pseudomonas aeruginosa* PA01 (Accession number NC_002516 REGION: 1895692 . . . 1896495) were cloned into plasmids and tested to determine if they could complement *E. coli* cysC or cysH knockout mutants, which are auxotrophic for both cysteine and methionine.

Briefly, the cysH genes from *Bacillus subtilis* 168 and *Pseudomonas aeruginosa* PA01 were transformed into BL21 (DE3)ΔcysH, a cysH knockout of BL21(DE3), to test for complementation. Single colonies from the following four strains were used to inoculate 5 mL cultures containing the Overnight Express medium (OnEX: defined medium supplemented with amino acids but not cysteine or methionine) from Novagen.

Cultures were incubated for 48 hrs at 30° C. with constant shaking. The results, presented in Table 14, indicate that both the cysH gene from *B. subtilis* and *P. aeruginosa* were able to complement the cysH knockout in *E. coli* and to sustain growth.

TABLE 14

Optical density at 600 nm of ΔcysH complementation experiments

| Strain | $OD_{600}$ |
| --- | --- |
| BL21(DE3) (wild type strain) | 5.2 |
| BL21(DE3)ΔcysH (with deletion of cysH) | 0 |
| BL21(DE3)ΔcysH + pET23BscysH (addition of *Bacillus* cysH) | 7.2 |
| BL21(DE3) Δ cysH + pET23PacysH (addition of *Pseudomonas* cysH) | 6.8 |

Similarly, a strain that had the cysC gene knocked out was used to test complementation by the *B. subtilis* and *P. aeruginosa* cysH genes. Strain BL21(DE3) ΔcysC was transformed with plasmids pET23a, pET23a+cysH (*B. subtilis*), and pET23a+cysH (*P. aeruginosa*), respectively. Single colonies of the above three strains together with BL21(DE3) were inoculated in 5 mL of OnEx medium containing amino acids except L-cysteine and L-methionine. The cells were cultured at 37° C. with shaking for 48 h and growth was measure by $OD_{600\ nm}$. The results, showed in Table 15, indicated that cysH-encoded APS reductase from both *B. subtilis* and *P. aeruginosa* could complement the cysC mutation on BL21 (DE3) which demonstrated that it was possible to bypass the formation of PAPS.

TABLE 15

Optical density at 600 nm of ΔcysC complementation experiments

| strain | $OD_{600\ nm}$[a] |
| --- | --- |
| BL21(DE3) | 4.5 |
| BL21(DE3) ΔcysC + pET23a | 0.0 |
| BL21(DE3) ΔcysC + pET23a + cysH (*B. subtilis*) | 2.5 |
| BL21(DE3) ΔcysC + pET23a + cysH (*P. aeruginosa*) | 4.2 |

[a]The results are the average of three cultures.

Overexpression of Enzymes in the Sulfur Assimilation Pathway

As described above, to increase the production of methionine it can be helpful to have a very efficient sulfur assimilation pathway. To facilitate direct sulfhydrylation of the acylhomoserine precursor, the availability of $SH_2$ is essential. All of the main genes of the sulfur assimilation pathway were cloned and overexpressed in the methionine production strain TF4076BJF. The genes overexpressed were:

cys PUWA: sulfate permease cysDN: ATP sulfurylase (EC 2.7.7.4)

CysCCys II: APS kinase and PAPS sulfotransferase (EC 2.7.1.25 and EC 1.8.4.8)

CysIJCysG: NADPH-Sulfite reductase (EC 1.8.1.2)

CysB: transcription activator

These genes were overexpressed in a strain containing the dual pathways metABC and metXY, and the methionine production was measured in our standard shake flask protocol. The aforementioned five groups of sulfate assimilating genes were respectively cloned into vector pCL-(Prmf) which was constructed by replacing the Plac promoter of plasmid pCL1920 with the promoter of *E. coli* rmf gene. The results obtained are shown in Table 16 below:

TABLE 16

Results from overexpression of various sulfur assimilation pathway enzymes

| Strains | OD | Met mg/L | Met/OD |
| --- | --- | --- | --- |
| TF4076BJF metYX (Lm) | 8.0 | 934 | 116 |
| TF4076BJF metYX (Lm) cysPUWA | 4.2 | 206 | 49 |
| TF4076BJF metYX (Lm) cysDN | 10.3 | 1271 | 123 |
| TF4076BJF metYX (Lm) cysCcysH | 9.9 | 1348 | 136 |
| TF4076BJF metYX (Lm) cysJIcysG | 7.7 | 1038 | 134 |
| TF4076BJF metYX (Lm) cysB | 9.4 | 425 | 45 |

Overexpression of the transport enzymes as well as the transcription regulator resulted in lower production of methionine and a significant drop in the amount of methionine per unit of cell mass. Increasing the activity of the sulfurylase, the APS kinase and the sulfotransferase, all resulted in increased methionine production per unit of cells as well as total methionine produced. Given that these increases are observed in a strain harboring two different plasmids, it can be expected that the results will be improved much further once expression of the enzymes is tuned and optimized.

Example 4

Exemplary Methionine Production Strains

As previously described, the various genetic modifications described herein can be made through incorporation of recombinant DNA sequences independent of the chromosome, or the recombinant DNA sequences can be incorporated into the production strain chromosome. The recombinant DNA sequences can be incorporated into the host cells as a single copy or in multiple copies.

i) A microorganism, such as *E. coli* ATCC #13070 or TF4076, is engineered to contain a functional deletion of thrB and metJ so that the genes are attenuated. This microorganism expresses the metX and metY genes, as well as a recombinant nucleic acid sequence which causes overexpression of the native metH gene. The expression of metX and metY introduces an additional pathway in *E. coli* and the overexpression of the native metH gene causes an increased flux of homocysteine to methionine.

ii) Another production strain is created by making the following modifications to the microorganism described in i). The microorganism described in i), is further modified by transforming the microorganism with a recombinant DNA molecule encoding an active metZ gene, such as the one from *Pseudomonas aeruginosa*.

iii) Yet another production strain is created by making the following modifications to the microorganism described in i). The microorganism described in i), is further modified to replace the native metA gene with a feedback inhibition resistant metA gene, such as those described in Example 3.

iv) Another production strain is created by making the following modifications to the microorganism described in iii). The microorganism described in iii) is transformed with an active metZ gene.

v) Another production strain is created by making the following modifications to the microorganism described in i). The microorganism described in i) which overexpresses the product of the metF gene is additionally modified to attenuate the transcriptional repressor gene lacI.

vi) Additional production strains are created by making the following modifications to any of the productions strains described herein. The production strains are engineered to overexpress the genes cysDN, cysIJ, or cysCH or combinations thereof to improve sulfur assimilation. Optionally, these production strains are additionally modified to replace the native cysC and cysH from *E. coli* with a single cysH gene from *P. aeurignosa* or *B. subtilis*.

vii) Another production strain is made by modifying any of the production strains described herein such that the methionine importer gene metD is attenuated.

What is claimed is:

1. An isolated *E. coli* for producing a detectable amount of methionine, the isolated *E. coli* comprising:

one or more first polypeptides comprising direct sulfhydrylation activity, wherein the one or more first polypeptides uses O-succinylhomoserine (OSHS) or O-acetylhomoserine (OAHS) as a substrate and is encoded by metZ, metY or a combination thereof;

one or more second polypeptides comprising transsulfuration activity, wherein the one or more second polypeptides is encoded by endogenous *E. coli* metB, metC or a combination thereof; and a third polypeptide comprising homoserine O-succinyltransferase activity, wherein the third polypeptide is encoded by feedback inhibition resistant metA comprising the amino acid sequence of SEQ ID NO: 2, 4, 6, 8, or 10,
wherein the direct sulfhydrylation activity arises from expression of an exogenous nucleic acid sequence of metZ, metY, or a combination thereof, and
wherein metZ is obtained from *Pseudomonas aeruginosa*, and metY is obtained from *Leptospira meyeri, Deinococcus radiodurans, Chloroflexus aurantiacus*, or *Pseudomonas aeruginosa*.

2. The isolated *E. coil* of claim 1, wherein at least one gene selected from metD, metK, metJ, thrB, serA, and combinations thereof, is attenuated.

3. The isolated *E. coli* of claim 1, wherein at least one gene selected from metA, metB, metC, metE, metY, metZ, metX, metH, cysPWUA, cysD, cysN, cysC, cysH, cysI, cysJ, cysG, csyK, cysM, and combinations thereof, is over-expressed.

4. A method of making methionine, comprising:
culturing the isolated *E. coli* of claim 1 under conditions that permit production of methionine; and
isolating the methionine.

5. The method of claim 4, wherein the isolated *E. coli* further comprises a polypeptide having homoserine O-acetyltransferase activity with an amino acid sequence having at least 90% sequence identity to SEQ ID NO: 44, 45, 46 or 47.

6. The method of claim 4, wherein the one or more first polypeptides comprises an amino acid sequence having at least 90% sequence identity to SEQ ID NO: 36, 37, 38 or 39.

7. The method of claim 4, wherein the one or more first polypeptides comprises an amino acid sequence comprising at least 90% sequence identity to SEQ ID NO: 40.

8. The method of claim 4, wherein the isolated *E. coli* further comprises at least one of an attenuated gene selected from metD, metK, metJ, thrB, serA, and combinations thereof and additional genetically engineered nucleic acid sequence changes resulting in a genetically engineered production strain, and wherein the genetically engineered production strain produces 10% more methionine compared to the microorganism without such changes.

9. The isolated *E. coli* of claim 1, wherein the one or more first polypeptides comprises a nucleic acid sequence having at least 90% sequence identity to SEQ ID NO: 44, 45, 46 or 47.

10. The isolated *E. coli* of claim 1, wherein the one or more first polypeptides comprises a nucleic acid sequence selected from the group consisting of SEQ ID NOs: 44, 45, 46 and 47.

11. The isolated *E. coli* of claim 1, wherein the one or more first polypeptides comprises an amino acid sequence having at least 90% sequence identity to SEQ ID NO: 36, 37, 38 or 39.

12. The isolated *E. coli* of claim 1, wherein the one or more first polypeptides comprise an amino acid sequence comprising at least 90% sequence identity to SEQ ID NO: 40.

* * * * *